US008163692B2

(12) United States Patent
Awasthi et al.

(10) Patent No.: US 8,163,692 B2
(45) Date of Patent: *Apr. 24, 2012

(54) PROTECTION AGAINST AND TREATMENT OF IONIZING RADIATION

(75) Inventors: Sanjay Awasthi, Arlington, TX (US); Sharad S. Singhal, Arlington, TX (US)

(73) Assignee: University of North Texas Health Science Center of Fort Worth, Fort Worth, TX (US)

( * ) Notice: Subject to any disclaimer, the term of this patent is extended or adjusted under 35 U.S.C. 154(b) by 147 days.

This patent is subject to a terminal disclaimer.

(21) Appl. No.: 12/460,781

(22) Filed: Jul. 24, 2009

(65) Prior Publication Data

US 2010/0124566 A1 May 20, 2010

Related U.S. Application Data

(60) Continuation-in-part of application No. 11/741,447, filed on Apr. 27, 2007, which is a division of application No. 10/713,578, filed on Nov. 13, 2003, now abandoned.

(60) Provisional application No. 60/425,814, filed on Nov. 13, 2002.

(51) Int. Cl.
*A61K 38/00* (2006.01)
(52) U.S. Cl. ........................................................ 514/2
(58) Field of Classification Search ........................ None
See application file for complete search history.

(56) References Cited

U.S. PATENT DOCUMENTS

| 6,750,015 | B2 * | 6/2004 | Horwitz et al. ............ 435/6.17 |
| 7,611,839 | B2 | 11/2009 | Twine et al. |
| 2002/0119156 | A1 | 8/2002 | Chen et al. |
| 2003/0138793 | A1 * | 7/2003 | Su et al. ............................ 435/6 |

OTHER PUBLICATIONS

Awasthi et al., "RLIP76 is a major determinant of radiation sensitivity", Cancer Res., 65(14):6022-6028 (2005).
Dainiak N., "Hematologic consequences of exposure to ionizing radiation", Exp. Hematol., 30(6):513-528 (2002).
Devi GR., "siRNA-based approaches in cancer therapy", Cancer Gene Ther., 13(9):819-829 (2006). Epub Jan. 20, 2006.
Iyer et al., "Effects of ionizing radiation in targeted and nontargeted cells", Arch. Biochem. Biophys., 376(1):14-25 (2000).
Kumar et a., "Gene manipulation through the use of small interfering RNA (siRNA): from in vitro to in vivo applications", Adv. Drug. Deliv. Rev., 59(2-3):87-100 (2007). Epub Mar. 20, 2007.
Singhal et al., "Depletion of RLIP76 sensitizes lung cancer cells to doxorubicin", Biochem. Pharmacol., 70(3):481-488 (2005).
Singhal et al., "Regression of lung and colon cancer xenografts by depleting or inhibiting RLIP76 (Ral-binding protein 1)", Cancer Res., 67(9):4382-4389 (2007).
Singhal et al., "Regression of melanoma in a murine model by RLIP76 depletion", Cancer Res., 66(4):2354-2360 (2006).
Singhal et al., "Regression of prostate cancer xenografts by RLIP76 depletion", Biochem. Pharmacol., 77(6):1074-1083 (2009). Epub Nov. 25, 2008.
US NRC published a fact sheet on biological effects of radiation (Dec. 2004, 9 pages).
Wagner et al., "Treatment of radiation exposure and contamination", Radiographics., 14(2):387-396 (1994).
Sanjay Awasthi et al, Biochemistry, 37:5231-523811998).
Sanjay Awasthi et al, Biochemistry, 37:5239-5248 (1998).
Sanjay Awasthi et al, Biochemistry, 39:9327-9334 (2000).
Ji-Zhong Cheng et al, Journal of Biological Chemistry, 276(441:41213-41223 12001).
Yusong Yang et al, Journal of Biological Chemistry, 274(44): 19920-19230 (2001).
Sanjay Awasthi et al, Biochemistry, 40:4159-4168 (2001).
Sanjay Awasthi et al, Drug Metabolism and Disposition, 30(12):1200-1210 (2002).
Sharad S. Singhal et al, International Journal of Oncology, 22:365-375 (2003).
Sanjay Awasthi et al, International Journal of Oncology, 22:713-720 (2003).
Sanjay Awasthi et al, International Journal of Oncology, 22:721-732 (2003).
Sanjay Awasthi et al, International Journal of Cancer, 106(5):635-646(2003).
Rajendra Sharma et al, International Journal of Cancer, 112:934-942 (2004).
Sanjay Awasthi et al, Cancer Research, 65(14):6022-6028 (2005).
David Stuckler et al, Cancer Research, 65(3):991-998 (2005).
Sushma Yadav et al. Biochemical and Biophysical Research Communications, 328:1003-1009 (2005).
Sharad S. Singhal et al, Biochemical Pharmacology, 70:481-488 (2005).
Rajendra Sharma et al, Archives of Biochemistry and Biophysics 391(2):171-179 (2001).
Abstract: Sanjay Awasthi et al, RLIP 76 Mediates Doxorubicin Transport and Resistance in Lung Cancer, 18th Annual Meeting of the International Society for Biological Therapy of Cancer (ISBTC), Bethesda, MD, Oct. 30-Nov. 2, 2003.
Abstract: S. Awasthi et al, Anti-RLIP76 Antibodies Induce Apoptosis and Enhance Doxorubicin Cytotoxicity in Lung Cancer Cells, American Association for Cancer Research, 92nd Annual Meeting, New Orleans, LA, Mar. 24-28, 2001.
Abstract: Sanjay Awasthi et al, Anti-RLIP76 Antibodies Induce Apoptosis in Lung Cancer Cells and Display Marked Synergy witn Doxorubicin, American Association for Cancer Research, 93rd Annual Meeting, San Francisco, CA, Apr. 6-10, 2002.
Abstract: S. Awasthi et al, Tyrphostin and Genistein Inhibit ATPase and transport activity of RLIP76 and increase doxorubicin toxicity in lung cancer cells, American Association of Cancer Research, 94th Annual Meeting, Washington, DC, Jul. 11-14, 2003.

(Continued)

Primary Examiner — Laura B Goddard
(74) Attorney, Agent, or Firm — DLA Piper LLP (US)

(57) ABSTRACT

Methods of preparing a proteoliposome comprise the step of contacting a liposome with an effective portion of RalBP1 to create a proteoliposome. RalBP1 is effective for the protection and treatment of mammals and the environment against the accumulation of toxic compounds, and prevents accumulation of one or more toxic compounds, reduces the concentration of toxic compounds, and protects against further contamination with one or more toxic compounds. In addition, RalBP1 is effective for the protection and treatment of mammals against the effects of ionizing radiation.

30 Claims, 19 Drawing Sheets

OTHER PUBLICATIONS

Abstract: S. Awasthi et al, RALPB1 is a major determinant of radiation sensitivity and glutathione-Conjugate transport, American Association for Cancer Research, 95th Annual Meeting, Orlando, FL, Mar. 27-31, 2004.

Abstract: Dilki Wickramarachchi et al, Identification of Membrane Anchoring Domains of RLIP76 Using Deletion Mutant Analysis, American Association of Cancer Research, 96th Annual Meeting Anaheim, CA, Apr. 16-20, 2005.

William T. Sause, Chest, 1 16(61:504S-508S (Dec. 1999 Supplement), 1999.

Sharad S. Singhal et al, ACTA Biochimica Polonica, vol. 48(2), pp. 551-562 (2001).

American Type Culture Collection (Tumor Cell Lines, 2001).

Sushma Yadav et al, Biochemistry 43:16243-16253 12004).

Sanjay Awasthi et al, BMC Neuroscience 6:61-71 (2005).

Sharad Singhal et al, FEBS Letters 579:4635-4641 (2005).

Abstract: Sanjay Awasthi et al, A Novel Mechanism of Drug Resistance in Epilepsy, Blood Brain Barrier Conference at Cleveland Clinic Foundation, Cleveland, OH, Nov. 2-3, 2004.

Abstract: Sanjay Awasthi et al, Targeting Multiple Signaling Pathways with RLIP76, Gordon Conference on Molecular Therapeutics of Cancer, Colby Sawyer College, New London New Hampshire, Jul. 20, 2005.

Wagner et al . (Radiographics 1994; 14: 387-396).

US NRC Fact Sheet "Biological Effects fo Ratiation" Dec. 2004, pp. 1-9.

Iyer et al. (Archives of Biochemistry and Biophysics 2000; 376: 14-25).

Dainiak et al. (Experimental Hematology 2002; 30: 513-528).

Awasthi et al. (Biochemistry 2001; 40: 4159-4168).

Awasthi et al. (Toxicol. Applied Phalen. 1999; 155: 215-226).

Awasthi et al. (Biochemistry 2000; 39: 9327-9334).

Awasthi et al. (Toxicol. Applied Pharm. 1999; 155: 215-226).

* cited by examiner

FIG. 2

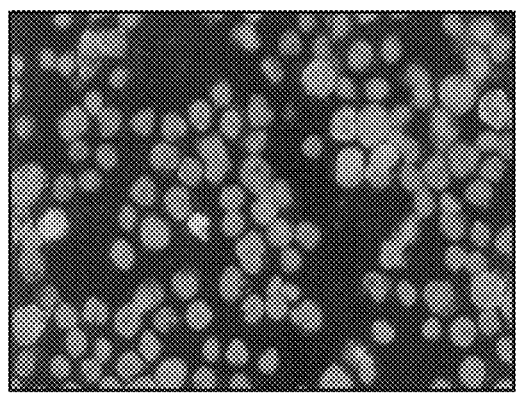
1. Control cells without heat shock treated with 4-HNE
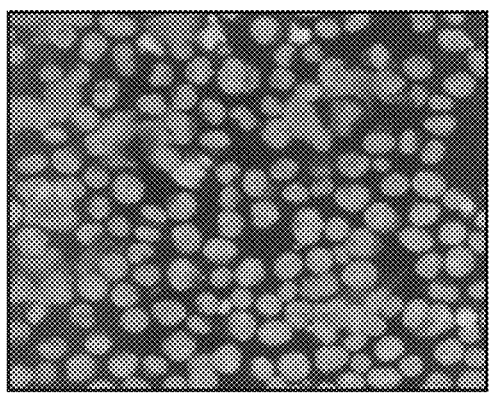
2. Heat shock preconditioned K562 cells
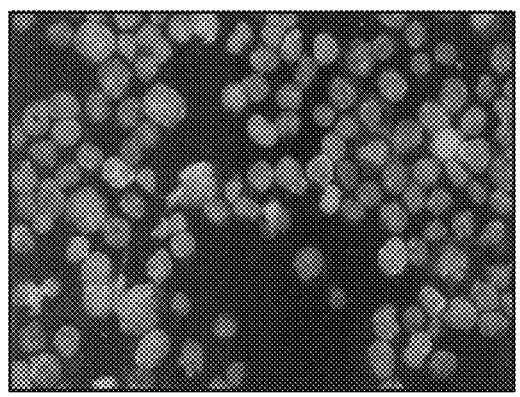
3. Heat shock preconditioned cells treated with 4-HNE
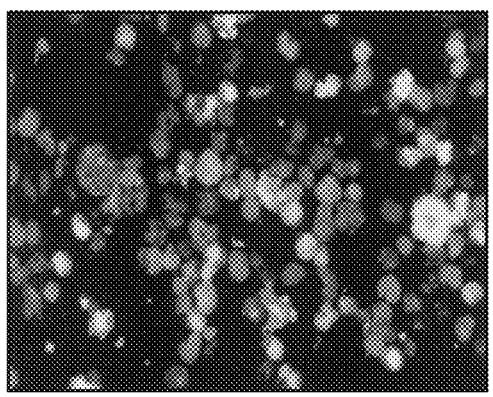
4. Heat shock preconditioned cells treated with 4-HNE after coating with anti-RLIP76 IgG
*FIG. 5*

| Organ | LOOH | | | | TBARS | | | | GSH | | | | GGCS | | | |
|---|---|---|---|---|---|---|---|---|---|---|---|---|---|---|---|---|
| | +/- | | -/- | | +/- | | -/- | | +/- | | -/- | | +/- | | -/- | |
| | M | F | M | F | M | F | M | F | M | F | M | F | M | F | M | F |
| Liver | - | - | ↓(0.77) ↓(0.79) | - | ↓(0.79) | - | ↓(0.47) ↓(0.60) | ↓(0.63) ↓(0.71) | - | ↓(0.86) | - | ↓(0.86) | ↑(3.63) | - | ↑(5.25) ↑(1.45) | ↑(1.16) |
| Lung | ↑(1.32) | ↑(1.23) | ↑(1.62) ↑(1.23) | ↑(1.96) ↑(1.59) | - | - | ↑(1.17) - | ↑(1.19) | ↑(1.41) | ↑(1.07) | - ↑(1.19) | - | - | - | - | - |
| Kidney | ↑(1.20) | ↑(1.18) | ↑(1.43) ↑(1.19) | ↑(1.53) ↑(1.29) | - | - | - ↑(1.06) | - | ↑(1.55) | ↑(1.77) | ↑(1.69) ↑(1.09) | ↑(1.88) - | ↓(0.65) | ↓(0.70) | ↓(0.57) ↓(0.85) | ↓(0.73) ↓(0.80) |
| Heart | ↑(1.47) | ↑(1.75) | ↑(3.12) ↑(2.12) | ↑(2.56) ↑(1.46) | ↑(1.26) | - | ↑(1.93) ↑(1.54) | ↑(1.54) ↑(1.35) | ↑(1.45) | ↑(1.31) | ↑(1.68) ↑(1.09) | ↑(1.41) - | ↓(0.68) | - | ↓(0.60) ↓(0.88) | ↓(0.54) ↓(0.78) |
| Brain | - | ↑(1.16) | ↑(1.32) ↑(1.25) | ↑(1.28) - | ↑(1.16) | ↑(1.16) | ↑(1.61) ↑(1.38) | ↑(1.46) ↑(1.26) | ↑(2.61) | ↑(2.48) | ↑(1.68) - | ↑(2.57) - | - | ↑(1.15) | - | ↓(0.27) ↓(0.67) |
| Intestine | ↑(1.56) | ↑(1.55) | ↑(2.13) ↑(1.48) | ↑(2.40) ↑(1.50) | ↑(1.60) | ↑(1.58) | ↑(2.95) ↑(1.84) | ↑(2.98) ↑(1.40) | - | ↑(1.91) | - ↑(1.22) | ↑(2.10) | ↓(0.72) | ↓(0.79) | ↓(0.58) ↓(0.80) | ↓(0.70) - |
| Spleen | ↑(1.63) | ↑(1.52) | ↑(2.99) ↑(1.83) | ↑(3.39) ↑(2.23) | ↑(1.46) | ↑(1.47) | ↑(2.54) ↑(1.73) | ↑(2.31) ↑(2.57) | - | - | - | - | ↓(0.68) | ↓(0.76) | ↓(0.49) ↓(0.72) | ↓(0.59) ↓(0.78) |
| | GST | | | | GPX | | | | GR | | | | G6PD | | | |
| Liver | ↑(1.26) | ↑(1.09) | ↑(1.54) ↑(1.22) | ↑(1.46) ↑(1.35) | ↑(1.41) | ↑(1.42) | ↓(1.60) ↓(1.13) | ↑(1.58) | - | ↓(0.86) | ↓(0.60) ↓(0.71) | ↓(0.71) ↓(0.53) | ↓(0.74) | ↓(0.72) | ↓(0.58) | ↓(0.75) |
| Lung | ↓(0.88) | - | - | ↓(0.90) | ↓(0.59) | ↓(0.75) | ↓(0.51) - | ↓(0.76) | ↓(0.68) | - | ↓(0.60) ↓(0.70) | ↓(0.87) - | ↓(0.75) | ↓(0.86) | ↓(0.43) ↓(0.57) | - |
| Kidney | ↓(0.79) | ↓(0.77) | ↓(0.67) ↓(0.86) | ↓(0.76) - | ↓(0.73) | ↓(0.72) | ↓(0.62) ↓(0.85) | ↓(0.68) | ↓(0.76) | ↓(0.72) | ↓(0.60) ↓(0.64) | ↓(0.87) - | ↓(0.62) | - | - | - |
| Heart | ↓(0.74) | ↓(0.78) | ↓(0.69) - | ↓(0.64) ↓(0.83) | ↓(0.31) | ↓(0.61) | ↓(0.07) ↓(0.22) | ↓(0.13) ↓(0.22) | ↓(0.60) | ↓(0.80) | ↓(0.70) ↓(0.92) | ↓(0.56) ↓(0.78) | - | - | ↓(0.59) | ↓(0.67) ↓(0.81) |
| Brain | - | ↓(0.75) | ↓(0.73) ↓(0.81) | ↓(0.63) ↓(0.81) | ↓(0.44) | ↓(0.73) | ↓(0.24) ↓(0.54) | ↓(0.41) ↓(0.56) | ↑(1.12) | - | ↓(0.52) ↓(0.87) | ↓(0.79) ↓(0.86) | - | - | ↑(1.60) ↑(1.50) | ↓(0.88) ↓(0.81) |
| Intestine | ↓(0.78) | - | - | ↓(0.78) ↓(0.87) | ↓(0.51) | ↓(0.65) | ↓(0.35) ↓(0.70) | ↓(0.48) ↓(0.15) | ↓(0.75) | ↓(0.78) | ↑(1.12) - | - | - | - | ↑(1.20) ↑(1.12) | ↓(0.85) - |
| Spleen | ↓(0.60) | ↓(0.63) | ↓(0.50) ↓(0.81) | ↓(0.62) - | ↓(0.46) | ↓(0.63) | ↓(0.38) - | ↓(0.49) ↓(0.79) | - | - | ↓(0.59) - | ↓(0.67) - | ↓(0.67) | ↓(0.87) | ↓(0.21) ↓(0.32) | ↓(0.81) - |

| Organ | LOOH +/- M | LOOH +/- F | LOOH -/- M | LOOH -/- F | TBARS +/- M | TBARS +/- F | TBARS -/- M | TBARS -/- F | GSH +/- M | GSH +/- F | GSH -/- M | GSH -/- F | GGCS +/- M | GGCS +/- F | GGCS -/- M | GGCS -/- F |
|---|---|---|---|---|---|---|---|---|---|---|---|---|---|---|---|---|
| Liver | - | - | - | - | - | - | ↓(0.57) ↓(0.71) | ↓(0.69) ↓(0.78) | - | - | - | - | ↑(3.93) | - | ↑(4.45) | ↑(1.36) ↑(1.35) |
| Lung | ↑(1.43) | ↑(1.37) | - | ↑(1.13) | - | ↑(1.28) | ↑(1.25) ↑(1.28) | ↑(1.35) ↑(1.39) | - | ↑(1.07) | ↑(1.38) ↑(1.16) | - | - | - | - | - |
| Kidney | ↑(1.44) | ↑(1.30) | ↑(1.67) ↑(1.27) | ↑(2.10) ↑(1.71) | - | - | ↑(1.11) | ↑(1.20) ↑(1.20) | ↑(1.14) | ↑(1.11) | ↑(1.34) | ↑(1.24) ↑(1.27) | ↓(0.84) | ↑(0.84) | ↓(0.72) | ↓(0.85) |
| Heart | ↑(2.24) | ↑(2.04) | ↑(1.43) ↑(1.19) | ↑(1.61) ↑(1.36) | ↑(1.00) | - | ↑(2.24) ↑(1.78) | ↑(1.76) ↑(1.53) | ↑(1.59) | ↑(1.82) | ↑(1.76) ↑(1.14) | ↑(2.07) ↑(1.17) | ↓(0.81) | - | ↓(0.65) | ↓(0.71) |
| Brain | ↑(1.25) | ↑(1.30) | ↑(3.35) ↑(2.28) | ↑(2.88) ↑(1.64) | ↑(1.40) | ↑(1.29) | ↑(2.17) ↑(1.86) | ↑(1.84) ↑(1.59) | ↑(1.79) | ↑(1.44) | ↑(2.07) ↑(1.43) | ↑(1.57) | - | - | - | ↓(0.77) |
| Intestine | ↑(1.80) | ↑(1.93) | ↑(1.35) ↑(1.28) | ↑(1.47) ↑(1.26) | ↑(1.80) | ↑(1.96) | ↑(3.39) ↑(2.11) | ↑(3.30) ↑(2.09) | ↑(2.93) | ↑(2.49) | ↑(3.02) ↑(1.15) | ↑(2.79) ↑(1.13) | ↓(0.83) | ↑(1.30) | ↓(0.71) | ↓(0.76) |
| Spleen | ↑(2.07) | ↑(2.16) | ↑(2.46) ↑(1.57) | ↑(2.48) ↑(1.60) | ↑(1.97) | ↑(1.78) | ↑(2.86) ↑(1.96) | ↑(2.69) ↑(1.83) | - | ↑(2.23) | ↑(1.27) | ↑(2.47) ↑(1.29) | ↓(0.61) | ↑(1.40) | ↓(0.46) ↓(0.68) | ↓(0.79) |

| Organ | GST +/- M | GST +/- F | GST -/- M | GST -/- F | GPX +/- M | GPX +/- F | GPX -/- M | GPX -/- F | GR +/- M | GR +/- F | GR -/- M | GR -/- F | G6PD +/- M | G6PD +/- F | G6PD -/- M | G6PD -/- F |
|---|---|---|---|---|---|---|---|---|---|---|---|---|---|---|---|---|
| Liver | ↑(1.31) | ↑(1.57) | ↑(1.84) ↑(1.46) | ↑(1.66) ↑(1.53) | ↑(1.47) | ↑(1.63) | ↑(1.65) ↑(1.17) | ↑(1.80) ↑(1.26) | - | - | ↓(0.77) | ↓(0.67) ↓(0.78) | ↓(0.78) | - | ↓(0.57) | ↓(0.53) |
| Lung | - | - | - | - | ↓(0.68) | ↓(0.80) | ↓(0.55) | ↓(0.73) | ↑(1.11) | - | ↓(0.61) ↓(0.71) | ↓(0.84) | ↓(0.77) | ↑(1.17) | ↓(0.44) ↓(0.51) | ↑(1.20) |
| Kidney | ↑(1.83) | ↓(0.86) | - | - | ↓(0.83) | ↓(0.74) | ↓(0.78) ↓(0.93) | ↓(0.76) | - | - | ↓(0.67) | - | - | ↑(1.23) | ↑(1.20) | ↑(1.19) ↑(1.41) |
| Heart | ↓(0.21) | ↓(0.78) | ↓(0.77) | ↓(0.73) | ↓(0.47) | ↓(0.72) | ↓(0.07) ↓(0.22) | ↓(0.17) ↓(0.28) | - | ↓(0.73) | ↓(0.76) | ↓(0.51) ↓(0.71) | - | ↑(1.16) | ↓(0.63) | ↑(1.25) ↑(1.50) |
| Brain | ↓(0.24) | ↓(0.80) | - | - | ↓(0.59) | ↓(0.73) | ↓(0.30) ↓(0.69) | ↓(0.45) ↓(0.62) | ↑(1.20) | - | ↓(0.58) | ↓(0.67) ↓(0.84) | ↑(1.47) | - | ↑(2.01) ↑(1.87) | - |
| Intestine | ↓(0.38) | - | ↓(0.67) ↓(0.86) | - | ↓(0.59) | - | ↓(0.37) ↓(0.71) | ↓(0.54) | - | - | ↑(1.09) | - | - | - | ↑(1.22) ↑(1.14) | - |
| Spleen | ↓(0.84) | ↓(0.69) | ↓(0.55) | ↓(0.73) | ↓(0.52) | ↓(0.63) | ↓(0.40) ↓(0.88) | ↓(0.53) ↓(0.85) | - | - | ↓(0.73) | ↓(0.75) | - | ↑(1.39) | ↓(0.23) ↓(0.34) | ↑(1.20) ↑(1.38) |

| Organ | DNTR | DXTR | LOOH | TBARS | G6PD | GGCS | GPX | GR | GSH | GST |
|---|---|---|---|---|---|---|---|---|---|---|
| Brain | | | G, GD, R | GD, G-R | R, G-GD | R, G-GD | GD-R, G-GD | G-GD, G-R, GD-R | G, GD, R | |
| Heart | G-GD, G-R | G-GD, G-R | R, G-GD | G, GD, R | THR | THR | R, G-GD | THR | G-GD, G-R | G, GD |
| Intestine | | | GD, G-R | G, GD, R | GD, R | GD, G-R | G-GD, G-R | GD, G-R | G, GD, R | G, GD, R |
| Kidney | | | G-GD, G-R | G-R | GD, R | G-GD, G-R | GD-R, G-GD | G-GD, G-R | | THR |
| Liver | | | G, GD, R | G, GD, G-R | G, G-R | G-GD | R, G-GD | G, GD | G, GD, R | R, G-GD |
| Lung | | | R, G-GD | G, GD, R | R, G-GD | | G-GD | G-GD, G-R | G, GD | R, G-GD |
| Spleen | | | GD-R, G-GD | G, GD, R | G-GD, G-R, GD-R | THR | G | G-GD, G-R | G, GD, R | G-GD, G-R |

G → Genotype main effect
GD → Gender main effect
R → Radiation main effect
G-GD → Genotype-Gender two way effect
G-R → Genotype-Radiation two way effect
GD-R → Gender-Radiation two way effect
THR → Three way effect (Gender-Genotype-Radiation)

SEQUENCE LISTING

```
<160> NUMBER OF SEQ ID NOS: 5

<210> SEQ ID NO 1
<211> LENGTH: 501
<212> TYPE: PRT
<213> ORGANISM: Artificial Sequence
<220> FEATURE:
<223> OTHER INFORMATION: Recombinant protein expressed in E. coli

<400> SEQUENCE: 1

Met Leu Pro Phe Leu Ser Met Leu Val Leu Leu Val Gln Pro Leu Gly
1               5                   10                  15

Asn Leu Gly Ala Glu Met Lys Ser Leu Ser Gln Arg Ser Val Pro Asn
            20                  25                  30

Thr Cys Thr Leu Val Met Cys Ser Pro Thr Glu Asn Gly Leu Pro Gly
        35                  40                  45

Arg Asp Gly Arg Asp Gly Arg Glu Gly Pro Arg Gly Glu Lys Gly Asp
    50                  55                  60

Pro Gly Leu Pro Gly Pro Met Gly Leu Ser Gly Leu Gln Gly Pro Thr
```

```
                65                  70                  75                  80
Gly Pro Val Gly Pro Lys Gly Glu Asn Gly Ser Ala Gly Glu Pro Gly
                        85                  90                  95
Pro Lys Gly Glu Arg Gly Leu Ser Gly Pro Gly Leu Pro Gly Ile
                100                 105                 110
Pro Gly Pro Ala Gly Lys Glu Gly Ser Gly Lys Gln Gly Asn Ile
                115                 120                 125
Gly Pro Gln Gly Lys Pro Gly Pro Lys Gly Glu Ala Gly Pro Lys Gly
                130                 135                 140
Glu Val Gly Ala Pro Gly Met Gln Gly Ser Thr Gly Ala Lys Gly Ser
145                 150                 155                 160
Thr Gly Pro Lys Gly Glu Arg Gly Ala Pro Gly Val Gln Gly Ala Pro
                165                 170                 175
Gly Asn Ala Gly Ala Gly Pro Ala Gly Pro Ala Gly Pro Gln Gly
                180                 185                 190
Ala Pro Gly Ser Arg Gly Pro Pro Gly Leu Lys Gly Asp Arg Gly Val
                195                 200                 205
Pro Gly Asp Arg Gly Ile Lys Gly Glu Ser Gly Leu Pro Asp Ser Ala
210                 215                 220
Ala Leu Arg Gln Gln Met Glu Ala Leu Lys Gly Lys Leu Gln Arg Leu
225                 230                 235                 240
Glu Val Ala Phe Ser His Tyr Gln Lys Ala Ala Leu Phe Pro Asp Gly
                245                 250                 255
Arg Ala Gln Met Asp Pro Asn Arg Ile Ser Glu Asp Ser Thr His Cys
                260                 265                 270
Phe Tyr Arg Ile Leu Arg Leu His Glu Asn Ala Gly Leu Gln Asp Ser
                275                 280                 285
Thr Leu Glu Ser Glu Asp Thr Leu Pro Asp Ser Cys Arg Arg Met Lys
                290                 295                 300
Gln Ala Phe Gln Gly Ala Val Gln Lys Glu Leu Gln His Ile Val Gly
305                 310                 315                 320
Pro Gln Arg Phe Ser Gly Ala Pro Ala Met Met Glu Gly Ser Trp Leu
                325                 330                 335
Asp Val Ala Gln Arg Gly Lys Pro Glu Ala Gln Pro Phe Ala His Leu
                340                 345                 350
Thr Ile Asn Ala Ala Ser Ile Pro Ser Gly Ser His Lys Val Thr Leu
                355                 360                 365
Ser Ser Trp Tyr His Asp Arg Gly Trp Ala Lys Ile Ser Asn Met Thr
                370                 375                 380
Leu Ser Asn Gly Lys Leu Arg Val Asn Gln Asp Gly Phe Tyr Tyr Leu
385                 390                 395                 400
Tyr Ala Asn Ile Cys Phe Arg His His Glu Thr Ser Gly Ser Val Pro
                405                 410                 415
Thr Asp Tyr Leu Gln Leu Met Val Tyr Val Lys Ser Ile Lys
                420                 425                 430
Ile Pro Ser Ser His Asn Leu Met Lys Gly Gly Ser Thr Lys Asn Trp
                435                 440                 445
Ser Gly Asn Ser Glu Phe His Phe Tyr Ser Ile Asn Val Gly Gly Phe
                450                 455                 460
Phe Lys Leu Arg Ala Gly Glu Glu Ile Ser Ile Gln Val Ser Asn Pro
465                 470                 475                 480
Ser Leu Leu Asp Pro Asp Gln Asp Ala Thr Tyr Phe Gly Ala Phe Lys
                485                 490                 495
```

Val Gln Asp Ile Asp
500

<210> SEQ ID NO 2
<211> LENGTH: 1974
<212> TYPE: DNA
<213> ORGANISM: Artificial Sequence
<220> FEATURE:
<223> OTHER INFORMATION: Human bone marrow cDNA library

<400> SEQUENCE: 2

| | | | | | |
|---|---|---|---|---|---|
| atgactgagt | gcttcctgcc | ccccaccagc | agccccagtg | aacaccgcag | ggtggagcat | 60 |
| ggcagcgggc | ttacccggac | ccccagctct | gaagagatca | gccctactaa | gtttcctgga | 120 |
| ttgtaccgca | ctggcgagcc | ctcacctccc | catgacatcc | tcatgagcct | cctgatgtag | 180 |
| tgtctgatga | tgagaaagat | catgggaaga | aaaaagggaa | atttaagaaa | aaggaaaaga | 240 |
| ggactgaagg | ctatgcagcc | tttcaggaag | atagctctgg | agatgaggca | gaaagtcctt | 300 |
| ctaaaatgaa | gaggtccaag | ggaatccatg | ttttcaagaa | gaagcccagc | ttttctaaaa | 360 |
| agaaggaaaa | ggattttaaa | ataaaagaga | acccaaaga | agaaaagcat | aagaagaaaa | 420 |
| gcacaaagaa | gaaaaacata | agagaagaa | gtcaaaagac | ttgacagcag | ctgatgttgt | 480 |
| taaacagtgg | aaggaaaaga | agaaaaagaa | aaagccaatt | caggagccag | aggtgcctca | 540 |
| gattgatgtt | ccaaatctca | aacccatttt | tggaattcct | ttggctgatg | cagtagagag | 600 |
| gaccatgatg | tatgatggca | ttcggctgcc | agccgttttc | cgtgaatgta | tagattacgt | 660 |
| agagaagtat | ggcatgaagt | gtgaaggcat | ctacagagta | tcaggaatta | aatcaaaggt | 720 |
| ggatgagcta | aaagcagcct | atgaccggga | ggagtctaca | aacttggaag | actatgagcc | 780 |
| taacactgta | gccagtttgc | tgaagcagta | tttgcgagac | cttccagaga | atttgcttac | 840 |
| caaagagctt | atgcccagat | tgaagaggc | ttgtgggagg | accacggaga | ctgagaaagt | 900 |
| gcaggaattc | cagcgtttac | tcaaagaact | gccagaatgt | aactatcttc | tgatttcttg | 960 |
| gctcattgtg | cacatggacc | atgtcattgc | aaaggaactg | gaaacaaaaa | tgaatataca | 1020 |
| gaacatttct | atagtgctca | gcccaactgt | gcagatcagc | aatcgagtcc | tgtatgtgtt | 1080 |
| tttcacacat | gtgcaagaac | tcttttggaaa | tgtggtacta | aagcaagtga | tgaaacctct | 1140 |
| gcgatggtct | aacatggcca | cgatgcccac | gctgccagag | acccaggcgg | gcatcaagga | 1200 |
| ggagatcagg | agacaggagt | ttctttttgaa | ttgtttacat | cgagatctgc | agggtgggat | 1260 |
| aaaggatttg | tctaaagaag | aaagattatg | ggaagtacaa | agaattttga | cagcccctcaa | 1320 |
| aagaaaactg | agagaagcta | aaagacagga | gtgtgaaacc | aagattgcac | aagagatagc | 1380 |
| cagtctttca | aaagaggatg | tttccaaaga | agagatgaat | gaaaatgaag | aagttataaa | 1440 |
| tattctcctt | gctcaggaga | atgagatcct | gactgaacag | gaggagctcc | tggccatgga | 1500 |
| gcagtttctg | cgccggcaga | ttgcctcaga | aaaagaagag | attgaacgcc | tcagagctga | 1560 |
| gattgctgaa | attcagagtc | gccagcagca | cggccgaagt | gagactgagg | agtactcctc | 1620 |
| cgagagcgag | agcgagagtg | aggatgagga | ggagctgcag | atcattctgg | aagacttaca | 1680 |
| gagacagaac | gaagagctgg | aaataaagaa | caatcatttg | aatcaagcaa | ttcatgagga | 1740 |
| gcgcgaggcc | atcatcgagc | tgcgcgtgca | gctgcggctg | ctccagatgc | agcgagccaa | 1800 |
| ggccgagcag | caggcgcagg | aggacgagga | gcctgagtgg | cgcggggtg | ccgtccagcc | 1860 |
| gcccagagac | ggcgtccttg | agccaaaagc | agctaaagag | cagccaaagg | caggcaagga | 1920 |
| gccggcaaag | ccatcgccca | gcagggatag | gaaggagacg | tccatctgad | aasv | 1974 |

-continued

```
<210> SEQ ID NO 3
<211> LENGTH: 146
<212> TYPE: DNA
<213> ORGANISM: Mouse

<400> SEQUENCE: 3
tttgttaaat tttctatctt ctgctcactc gtcccttaac agttgctgtt aataagggg       60 acagtataca ctagaccctg ttacagtgca gttatagaat gtcacatttt taaagttgac    120
tctgcctgca gggcttgctt taggta                                         146

<210> SEQ ID NO 4
<211> LENGTH: 250
<212> TYPE: DNA
<213> ORGANISM: Mouse

<400> SEQUENCE: 4
tgctatttta ctttgccaag atgctggaag ctgagtggga aacaagttgt agagctcagt     60 ggggggagg ccaatgagaa gtttgcttgt tagactaagc cccggccata ggggaaggta    120
agtcaaagat taaggctgat gatttataag gaaaaatcca aaggagtcaa gtgtgggtta   180
agtacacctt aatgatgtta gtaggtttaa gaggattaat tatgtaacag ctcagttagg   240
taataattgg                                                           250

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
aaatggcgtt acttaagcta gcttgc                                         26
```

PROTECTION AGAINST AND TREATMENT OF IONIZING RADIATION

CROSS REFERENCES TO RELATED APPLICATIONS

This application is a continuation-in-part of U.S. patent application Ser. No. 11/741,447, filed Apr. 27, 2007, which is a divisional of U.S. patent application Ser. No. 10/713,578 filed Nov. 13, 2003, now abandoned, which claims the benefit of U.S. Provisional Patent Application No. 60/425,814, filed Nov. 13, 2002, each of which are incorporated herein by reference in their entirety.

STATEMENT REGARDING FEDERALLY SPONSORED RESEARCH OR DEVELOPMENT

This invention was made with government support under CA 77495 awarded by the National Institutes of Health. The government has certain rights in the invention.

REFERENCE TO A SEQUENCE LISTING

This application incorporates by reference sequence listing material included on computer readable form and identified as 124263-1073 SEQ.ST25.txt saved on Apr. 27, 2007, in ASCII readable form.

BACKGROUND OF THE INVENTION

The present invention relates to the bioremediation (e.g., removal) of toxic compounds, and more specifically to the protection of mammals and the environment against toxic organic compounds, their related species and metabolites, especially those that result from damage or stress.

Toxic compounds can harm both humans and the environment. Toxic compounds are often referred to as xenobiotics. These compounds are generally highly toxic to life forms (including humans), are exceedingly difficult to dispose of, and are of major concern to industry (because of the cost and/or difficulty of treatment) and to regulatory agencies. Toxic compounds may be by-products of larger molecules, or may result from damage to biological molecules (e.g., stress that is drug-induced, chemically-induced, or physiologically induced). The damage may also be physiologic in nature (e.g., the result of an oxidative or alkylating nature) or be produced by radiation.

In the environment, a large source of xenobiotics arises from the manufacturing of chemicals (e.g., benzene, toluene, styrene, pesticides, dioxins, halogenated organic compounds such as pentachlorophenol and PCB, and polybrominated diphenyl ethers). Toxic environmental pollutants are often present in process waste streams, and may be present in larger quantities after spills, or in the soil and water associated with abandoned or poorly controlled industrial sites.

Environmental toxic compounds, whether in process waste streams or in spills, are now generally treated by physical, chemical or biological means. One means includes trying to physically remove the toxic materials, e.g., from air and water streams, by contacting the toxins with activated carbon particles contained within adsorption columns. A significant drawback of this approach is that the xenobiotics adsorbed onto the carbon are not destroyed, only physically removed from the contaminated stream, and therefore some subsequent disposal method to destroy the toxins must still be employed. Toxic organic compounds may also be removed by chemical means (e.g., incineration); however, this approach is costly (e.g., high temperature and pressure equipment are required) and results in the release of undesirable combustion products into the atmosphere. Therefore, there remains a need to cost-effectively process environmental toxic organic compounds without adding environmental insults or wastes into the surroundings.

Biological treatment of toxic compounds often involves the addition of the toxic material to bioreactors (i.e., tanks with aqueous microorganism suspensions) to degrade the materials to harmless end products such as carbon dioxide and water. Although potentially the lowest cost approach to xenobiotic destruction, current biological treatment of toxic organics suffers from fundamental inefficiencies. For example, the toxic material often kills the microorganisms (this is especially common with conventional wastewater treatment systems). Another drawback is that when added too slowly, microorganisms present in a biotreatment system often starve or become unable to consume the toxic compounds. Because of the above problems with current bioremediation there still remains a long-felt need to transform these toxic compounds in a more efficient, controlled, and cost-effective manner.

In mammals, toxic compounds may arise from environmental contact, from ingestion or infusion of organic or inorganic chemicals (including pharmaceutical and herbal products), and from internal oxidative damage or stress, alkylating damage, or radiation damage. Environmental contaminants, poisons, allergy producing agents and chemicals (such as pesticide residues), toxic trace elements, certain drugs and pharmaceuticals, as well as excessive levels of other non-end product metabolites that are formed in biochemical reactions in the body during states of altered metabolism are examples of compounds that may produce toxic organic compounds. Mammalian syndromes, conditions, and diseases may also lead to the accumulation of these toxic compounds, examples of which include fatigue, cancer, hypotonia, depression, lassitude, muscle weakness, insomnia, recurring bad dreams, intestinal complaints (myalgia), confusion, and functional nervous system problems.

Most mammals contain intrinsic biotransformation-detoxification pathways to rid themselves of naturally occurring toxic organic compounds; however, these physiologic pathways are only efficient when biotransformation-detoxification requirements are small. Under situations of stress (e.g., oxidative, alkylating, radiation) or when nonnatural chemicals are introduced, natural biotransformation-detoxification pathways are, themselves, often incapable, inefficient and ineffective at ridding the cell or the biologic system of the chemical. Often, the chemical may be initially transformed after which potentially toxic by-products then accumulate within the host and can prove fatal. Attempts to protect mammals from toxic accumulation of organic compounds and their by-products are generally done after chemical insult has already occurred. The addition of chemicals, foods, vitamins, nutritional supplements or drugs may be used to try to relieve the body of the excessive toxins. Most of the additives, however, are either inefficient, costly and/or have serious deleterious side effects. For mammals, these current inefficiencies and problems mean that there remains a need to aid in the protection of mammals against toxic organic compounds in an efficient, controlled, and cost-effective manner.

SUMMARY OF THE INVENTION

The present invention solves the current problems associated with removal of toxic wastes (e.g., toxic waste compounds, xenobiotics) from the environment, from biologic waste, and from mammals. As identified herein is a novel protein that is a non-ABC transporter, referred to herein as RLIP76 and with an official human genome name of ralA binding protein also referred to herein as RalBP1, that efficiently detoxifies xenobiotics by a process that catalyzes ATP. Importantly, the protein is useful in the protection of mammals against xenobiotic accumulation and for the transport of xenobiotic waste in the environment often associated with industrial and chemical processing. RalBP1 is also identified as a protein involved in drug resistance and in the protection against toxic by-products of metabolism, stress, and drugs or other organic chemicals.

Generally, and in one form, described herein is a method of preparing a proteoliposome comprising the step of contacting a liposome with an effective portion of RalBP1 to create a proteoliposome. The liposome is generally selected at least from the group consisting of lectin, glycolipid, phospholipid, and combinations thereof. In another aspect, the proteoliposome is added to one or more toxic compounds to reduce the concentration of toxic compounds, prevent the accumulation of toxic compounds, and protect against further contamination with one or more toxic compounds. Toxic compounds may be present in an organism, mammalian cell, transfected mammalian cell, bioreactor, soil, water, spill, process waste stream, manufacturing waste chemical waste, laboratory waste, hospital waste, and combinations thereof, to which the proteoliposome is then added.

In another form, described herein is a proteoliposomal composition comprising a liposome and an effective portion of RalBP1. The proteoliposome is used to reduce the concentration of toxic compounds and may further comprise at least 4-hydroxynonenal, leukotriene, polychlorinated biphenyls, glutathione, and combinations thereof. The effective portion of RalBP1 is dependent on ATP for optimal activity. As discussed, the proteoeliposomal composition is generally used for the treatment of toxic compound exposure, is capable of being transfected into a mammalian cell, and is capable of having antibodies generated against it. The composition may be applied or administered to an organism in need thereof by injection, dermal delivery, infusion, ingestion, and combinations thereof and capable of producing the desired effects.

In yet another form, described herein is a method of reducing the effects of ionizing radiation comprising the step of adding a proteoliposome to a material with ionizing radiation, wherein the proteoliposome is a liposome and an effective portion of RalBP1. Alternatively, the proteoliposome may be added before the ionizing radiation. Ionizing radiation may include x-ray radiation, gamma radiation, ultraviolet radiation, thermal radiation, nuclear radiation, and combinations thereof.

Another embodiment is a kit prepared for using the proteoliposomal composition described above comprising an effective dose of a proteoliposome, wherein the proteoliposome is a liposome and an effective portion of RalBP1 and an instructional pamphlet. The kit is generally used to reduce the concentration of toxic compounds and their by-products and to enhance resistance to toxic compounds.

The benefits of RalBP1 include the environmental, chemical and biologic protection against toxic compounds and xenobiotics. RalBP1 is critical in the transport of toxic compounds and xenobiotics and for enhancing resistance to drugs/chemicals and their toxic by-products (e.g., chemotherapy and radiation therapy). As used herein, toxic compounds arise as by-products of chemical and manufacturing processes (e.g., waste products), metabolism, pathologic conditions, stress, radiation, and drugs/chemicals, as examples.

Certain embodiments of the present disclosure are directed to methods of preventing or treating radiation exposure in a mammal, comprising administering an effective amount of RLIP76 protein or an effective portion thereof to the mammal, wherein the RLIP76 protein or an effective portion thereof is administered one or more times to the mammal prior to the radiation exposure. The RLIP76 protein or an effective portion thereof may be comprised within a liposome, for example as a proteoliposomal composition comprising an effective portion of an RLIP76 protein. In certain embodiments, the RLIP76 protein or an effective portion thereof is administered to the mammal one or more times within 24 hours of radiation exposure. For example the RLIP76 may be administered to the mammal one or more times at 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours before or after radiation exposure.

In still other embodiments, the RLIP76 protein or an effective portion thereof is administered to the mammal one or more times prior to the radiation exposure, and one or more times after radiation exposure, for example within 24 hours or more than 24 hours after radiation exposure, or within 24 hours and more than 24 hours after radiation exposure. In embodiments where RLIP76 is administered to the mammal one or more times prior to radiation exposure, and one or more times after radiation exposure, the RLIP76 can be administered one or more times at about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 36 hours, 42 hours, 48 hours, 60 hours, 3 days, 3.5 days, 4 days, 4.5 days, 5 days, 5.5 days, 6 days, 6.5 days, 7 days, 7.5 days, 8 days, 8.5 days, 9 days, 9.5 days, 10 days, 10.5 days, 11 days, 11.5 days, 12 days, 12.5 days, 13 days, 13.5 days, 2 weeks, 3 weeks, 4 weeks, 5 weeks, 6 weeks, 7 weeks, 8 weeks or longer before or after radiation exposure.

An embodiment of the present disclosure is a method of preventing or treating the effects of exposure to ionizing radiation in a mammal in need of such prevention or treatment, comprising administering an effective amount of RLIP76 protein or an effective portion thereof to the mammal within 24 hours of exposure to the ionizing radiation. Another embodiment of the present disclosure is directed to a method of preventing or treating the effects of exposure to ionizing radiation in a mammal in need of such prevention or treatment, comprising administering one or more doses of a proteoliposomal composition comprising an effective amount of RLIP76 protein or an effective portion thereof to the mammal within 24 hours of exposure to the ionizing radiation. Yet another embodiment of the present disclosure is directed to a method of preventing or treating the effects of exposure to ionizing radiation in a mammal in need of such prevention or treatment, comprising administering (a) at least a first dose of a proteoliposomal composition comprising an effective amount of RLIP76 protein or an effective portion thereof to the mammal before exposure to the ionizing radiation, and (b) at least a second dose of a proteoliposomal composition comprising an effective amount of RLIP76 protein or an effective portion thereof to the mammal after exposure to the ionizing radiation.

The mammal may be, for example, a human. In certain embodiments, the ionizing radiation is x radiation, gamma radiation, ultraviolet radiation, thermal radiation, nuclear radiation, or a combination thereof. In some embodiments, the RLIP76 protein or an effective portion thereof is comprised within a liposome, for example a proteoliposome or a lipid encapsulated proteoliposome.

In certain embodiments, the RLIP76 protein or an effective portion thereof is administered within 24 hours before the exposure to the ionizing radiation. In other embodiments, the RLIP76 protein or an effective portion thereof is administered within 24 hours after the exposure to the ionizing radiation. In still other embodiments, the RLIP76 protein or an effective portion thereof is administered at about the time of the exposure to the ionizing radiation. The RLIP76 protein or an effective portion thereof as disclosed herein may be administered in one or more doses to the mammal. For example, any of these embodiments can be combined such that the RLIP76 protein is administered multiple times to the mammal in various combinations, including but not limited to within 24 hours before the exposure to the ionizing radiation, within 24 hours after the exposure to the ionizing radiation, and/or at about the time of the exposure to the ionizing radiation.

In certain embodiments, at least a first dose of the RLIP76 protein or an effective portion thereof is administered within 24 hours before the exposure to the ionizing radiation. In other embodiments, at least a first dose of the RLIP76 protein or an effective portion thereof is administered within 24 hours after the exposure to the ionizing radiation. In still other embodiments, at least a first dose of the RLIP76 protein or an effective portion thereof is administered at about the time of the exposure to the ionizing radiation. Each of these embodiments of the present disclosure may further comprise administering to the mammal at least a second dose of the RLIP76 protein or an effective portion thereof, for example within 24 hours after the exposure to the ionizing radiation or more than 24 hours after the exposure to the ionizing radiation. Each of these embodiments may also further comprise administering to the mammal at least a third dose of a proteoliposomal composition comprising an effective amount of RLIP76 protein or an effective portion thereof to the mammal, for example within 24 hours after the exposure to the ionizing radiation or more than 24 hours after the exposure to the ionizing radiation.

In other embodiments of the present disclosure, the RLIP76 protein or an effective portion thereof is administered in one or more doses to the mammal within 24 hours before the exposure to the ionizing radiation. This embodiment of the present disclosure may further involve administering to the mammal one or more doses of the RLIP76 protein or an effective portion thereof within 24 hours after the exposure to the ionizing radiation, or more than 24 hours after exposure to the ionizing radiation.

In each of the relevant above embodiments, the first dose, the second dose, and/or the third dose may comprise about the same amount of the RLIP76 protein or an effective portion thereof, or may comprise different amounts of the RLIP76 protein or an effective portion thereof. In some embodiments, for example, the first dose and the second dose may be administered at +1 hour and +12 hours after radiation exposure, respectively; +1 hour and +24 hours after radiation exposure, respectively; +12 hours and +24 hours after radiation exposure, respectively; +12 hours and +36 hours after radiation exposure, respectively; +12 hours and +48 hours after radiation exposure, respectively; +14 hours and +24 hours after radiation exposure, respectively; +14 hours and +36 hours after radiation exposure, respectively; or +14 hours and +48 hours after radiation exposure, respectively. In other embodiments, for example, the first dose, the second dose, and the third dose may be administered at +1 hour, +12 hours, +24 hours after radiation exposure, respectively; +4 hour, +12 hours, +24 hours after radiation exposure, respectively; +8 hour, +16 hours, +24 hours after radiation exposure, respectively; −24 hours before and +1 and +24 hours after radiation exposure, respectively; −24 hours before and +12 and +24 hours after radiation exposure, respectively; −1 hours before and +12 and +24 hours after radiation exposure, respectively; or −1 hour before and +24 and +48 hours after radiation exposure, respectively. Further additional doses of RLIP76 protein or an effective portion thereof may also be administered to the mammal in need thereof, in the same manner as described herein for the first three doses.

The RLIP76 protein or an effective portion thereof may be administered to a mammal in need thereof as disclosed herein at a dosage of between about 0.5 mg/kg body weight and about 14.0 mg/kg body weight, for example about 1.0 mg/kg body weight, about 1.5 mg/kg body weight. about 2.0 mg/kg body weight, about 2.5 mg/kg body weight, about 3.0 mg/kg body weight, about 3.5 mg/kg body weight, about 4.0 mg/kg body weight, about 4.5 mg/kg body weight, about 5.0 mg/kg body weight, about 5.5 mg/kg body weight, about 6.0 mg/kg body weight, about 6.5 mg/kg body weight, about 7.0 mg/kg body weight, about 7.5 mg/kg body weight, about 8.0 mg/kg body weight, about 8.5 mg/kg body weight, about 9.0 mg/kg body weight, about 9.5 mg/kg body weight, about 10.0 mg/kg body weight, about 10.5 mg/kg body weight, about 11.0 mg/kg body weight, about 11.5 mg/kg body weight, about 12.0 mg/kg body weight, about 12.5 mg/kg body weight, about 13.0 mg/kg body weight, or about 13.5 mg/kg body weight.

The RLIP76 protein or an effective portion thereof as disclosed herein may be administered in a pharmaceutical composition or proteoliposomal composition. In other embodiments, the pharmaceutical composition or proteoliposomal composition further comprises a lectin, a glycolipid, a phospholipid, an antioxidant, or a combination thereof. In other embodiments, the RLIP76 protein or an effective portion thereof is a recombinant protein or a portion thereof. The pharmaceutical composition or proteoliposomal composition of the present disclosure may be administered subcutaneously, intravenously, topically, orally, non-orally, or a combination thereof.

Those skilled in the art will further appreciate the above-noted features and advantages of the invention together with other important aspects thereof upon reading the detailed description that follows in conjunction with the drawings.

BRIEF DESCRIPTION OF THE DRAWINGS

For more complete understanding of the features and advantages of the present invention, reference is now made to the detailed description of the invention along with the accompanying figures.

FIG. 2 depicts human RalBP1 cDNA nucleotide sequence (SEQ ID NO:1), deduced amino acid sequence (SEQ ID NO:2) and peptide characterization.

FIG. 5 depicts the effect of anti-RalBP1 IgG on 4-HNE mediated apoptosis in heat shock pre-conditioned cells.

FIG. 11 depicts tissue-specific effects of RIP1 knockout on parameters reflecting oxidative stress in un-irradiated animals;

FIG. 12 depicts tissue-specific effects of RIP1 knockout on parameters reflecting oxidative stress in X-irradiated animals; and FIG. 13 depicts sample results of one way, two way and three way interactions of gender, genotype and radiation by ANOVA.

In FIG. 17, a complex of RLIP76 protein, liposomes, and the antioxidant BHT is designated TO-80Cx (the 80 refers to the mean size of the liposomes of 80 nm, which classifies them as intermediate sized vesicles); TO-80LA refers to the liposomes constituted in buffer with BHT but without RLIP76 protein. Times are in reference to hours before or after radiation exposure and the dose of 50 μg is the amount of RLIP76 protein contained in the total volume of TO-80Cx delivered with each dose. This amount represents a dose of 1.67 mg RLIP76 protein per kilogram of body weight of each mouse. The x-axis is the measure in days after radiation exposure and the y-axis is the percentage of each cohort alive on that day.

DETAILED DESCRIPTION OF THE INVENTION

Figure 1:
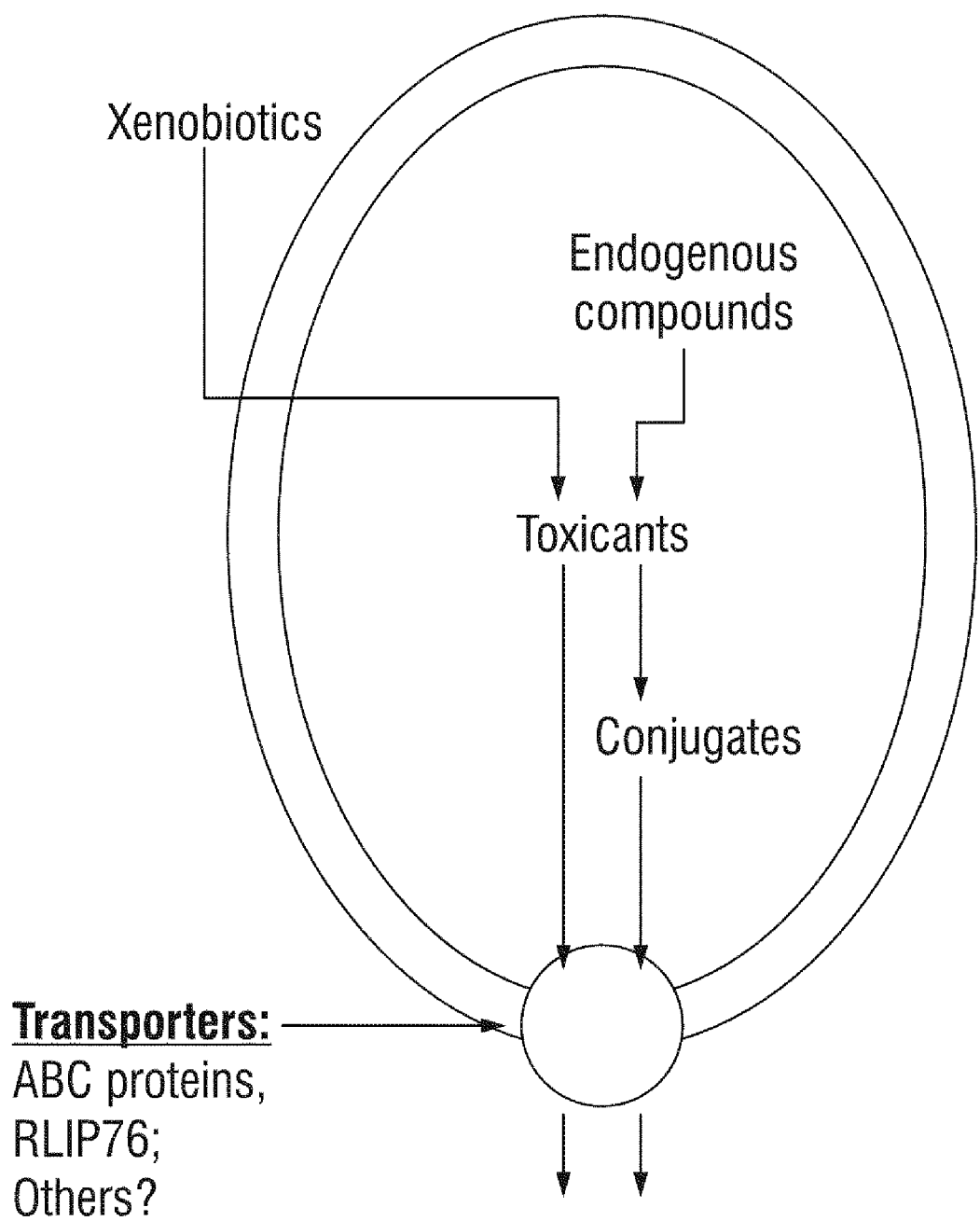
FIG. 1 is a schematic representation of the pathway of detoxification mechanisms of xeno- and endobiotics showing the role of a transporter such as RalBP1.

Although making and using various embodiments of the present invention are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

In the description which follows like parts may be marked throughout the specification and drawing with the same reference numerals, respectively. The drawing figures are not necessarily to scale and certain features may be shown exaggerated in scale or in somewhat generalized or schematic form in the interest of clarity and conciseness.

As used herein, a "proteoliposome" is generally a protein and lectin or glyco- or phospholipid combination that forms a spherical micellular-like or vesicular structure. The structures may form spontaneously or by chemical or mechanical manipulation, or combinations thereof. Proteoliposomes take advantage of the amphipathic nature of the lipid (or lectin) that causes them to form bilayers when in solution resulting in at least one of several shapes, including: (a) spherical micelle with the tails inward, or (b) bimolecular sheets that are bilayers with hydrophobic tails sandwiched between hydrophilic head groups. In general proteoliposomes may reseal themselves when torn or broken. Proteoliposomes may contain only one lectin or lipid or a variety and combination of each. Examples of phospholipids include phosphatidylcholine, sphingomyelin, phosphatidylserine, inositol phospholipids, and phosphatidylethanolamine. When used, proteoliposomes may be charged or electrically neutral and are generally used at physiological pH. They may also be structures mixed with detergent (e.g., detergent/lipid/protein, detergent/lectin/protein). Methods for preparing proteoliposomes of defined lipid-protein or lectin-protein ratios and size are well-known to one of ordinary skill in the art of molecular biology and protein/lipid biochemistry.

"Toxic compounds" as used herein may xenobiotics, radiation, toxins, waste products, by-products of larger organic or inorganic molecules and/or may result from damage to such molecules. Stress is one example of damage. Other damages may be environmentally-induced, metabolically-induced, drug-induced, chemically-induced, radiation-induced, and physiologically-induced, as examples. The toxic compounds may be in a mammal or occur in the environment or come from manufacturing and/or chemical processes that produce waste products. Toxic compounds, "toxic organic chemicals," and "xenobiotics" are often used interchangeably. Toxic compounds may also include crude oil, crude oil fraction, an organic or inorganic chemical compound, radiation, a chemical solvent, metabolite, metabolic by-product, a chemical warfare agent, drug, drug by-product, chemical by-product, and combinations thereof.

As used herein, an "antibody" is an immunoglobulin, a solution of identical or heterogeneous immunoglobulins, or a mixture of immunoglobulins.

The term "protein," as used herein, is meant to include any chain of amino acids and includes peptides, polypeptides, proteins, recombinant proteins, and modified proteins, such as glycoproteins, lipoproteins, phosphoproteins, metalloproteins, and the like.

As used herein, "an effective portion of —RalBP1," is any combination of proteolytic peptide products of RalBP1 that, when combined, promotes the transport or prevents the accumulation of toxic organic compounds and/or enhances resistance to the toxic compounds. The effective portion may be a recombinant RalBP1.

Any conventional eukaryotic or bacterial expression vectors, of which many are known in the art, may be used in the practice of this invention to transfect mammalian cells or bacterial cells with the claimed proteoliposome. "Transfection" as used herein, may refer to the incorporation of a nucleic acid or protein into a cell by any means readily known in the art of molecular biology. As examples, transfection may include incorporation by proteoliposomes, electroporation, by viral incorporation, or by a nucleic acid-containing structures (e.g., expression vector or plasmid) and combinations thereof. The eukaryotic cell expression vectors described herein may be synthesized by techniques well-known to those skilled in this art. The components of the vectors such as the bacterial replicons, selection genes, enhancers, promoters, and the like may be obtained from natural sources or synthesized by known procedures. Expression vectors useful in practicing this invention may also contain inducible promoters or comprise inducible expression systems as are well-known in the art. The expression vectors may be introduced into the host cells by purely conventional methods, of which several are known in the art.

The terms "mammal" or mammalian" and "organism" are often used interchangeably throughout the discussion of the present invention.

All technical and scientific terms used herein have the same meaning as commonly understood by one of ordinary skill in the art to which this invention belongs, unless defined otherwise. All publications mentioned herein are incorporated herein by reference to disclose and describe the methods and/or materials in connection with which the publications are cited.

Bioremediation

The bioremediation or removal of toxic compounds or xenobiotics in mammals is traditionally classified into two phases—Phase I and Phase II—and the detoxification process is often classified as Phase III. Phase I reactions are those catalyzed by enzymes including cytochrome P450, epoxide hydrolases, esterases, and amidases. These enzymes introduce/expose reactive groups in xenobiotics that create bioactivated metabolites that can then be conjugated to hydrophilic compounds, such as glutathione (GSH), glucuronate, sulfate, etc., by Phase II enzymes. Phase II reaction products must eventually be transported to complete the detoxification process (Phase III) because accumulation of these products can cause not only toxicity but can inhibit Phase II reactions. Hence, transport mechanisms designated as Phase III are an essential component of mammalian cellular defense mechanisms against toxic chemicals or xenobiotics (shown schematically in FIG. 1).

Both Phase I and Phase II biotransformation enzymes occur as members of multiple gene "superfamilies" that have been extensively characterized (e.g., CYP450s and glutathione S-transferases). In contrast, relatively little is known about the transporters comprising Phase III of the detoxification process. Some of the transporters may belong to several superfamilies or a small family specific to eukaryotic organisms; however, these molecules are not well understood physiologically or functionally. Known transporters are ABC transporters particularly P-glycoprotein (Pgp) and the multidrug resistance associated protein (MRP1). Little is understood about any other molecules that comprise the Phase III enzymes involved in the detoxification process.

The present invention has identified a non-ABC transporter, RalBP1, as a novel protein that efficiently detoxifies xenobiotics. While the protein has reported GTPase activity, the present invention discloses that RalBP1 is involved in the catalysis ATP. As presented herein, RalBP1 catalyzes ATP-dependent uphill transport of xenobiotics and their by-products. Its activity is stimulated by chemotherapeutic agents and is found to have two ATP-binding sequences that, when mutated, abrogate the ATP-binding, ATPase activity and transport function of the protein. RalBP1 may be reconstituted in proteoliposomes and mediates ATP-dependent saturable transport of xenobiotics and their by-products. Furthermore, transfection of the RalBP1 protein into mammalian cells confers resistance to chemotherapeutic agents. Cells enriched with RalBP1 also acquire resistance to xenobiotic toxicity. In addition, RalBP1 catalyzes the transport of physiologic ligands such as leukotrienes (LTC4) and the conjugate of 4-hydroxynonenal (4-HNE) and glutathione.

Transporters of the ABC Family

ABC transporters utilize the free energy of ATP hydrolysis to translocate substrates or allocrites across the membrane, and have Walker motifs (ATP binding sites) and transmembrane domains in their sequences. Overexpression of ABC transporters has been linked with drug resistance of certain bacteria, parasites and human cancer cells. Two ABC transporter family members P-glycoprotein (Pgp or MDR1) and multidrug resistance associated protein (MRP1) are characterized with respect to this function. Overexpression of Pgp, MRP1, or both is observed in many cancer cell lines exhibiting the multidrug resistance phenotype. Pgp overexpressing cancer cells exposed to a drug such as a chemotherapeutic agent (e.g., adriamycin, vinblastine, colchicines) show decreased accumulation of the drug.

MRP, now designated as MRP1 (first characterized member of the MRP family) or ABCC1 was originally cloned from a drug resistant line selected for doxorubicin (DOX) resistance. MRP1-mediated transport of the conjugates of GSH, glucuronate, and sulfate has been clearly demonstrated. MRP1 also mediates the transport of physiological GSH-conjugates (e.g., leukotrienes, GS-HNE-GSH conjugate of lipid peroxidation end product, 4-FINE). Transport of vincristine by MRP1-rich membrane vesicles has been demonstrated and this transport has been suggested to be linked to GSH co-transport.

Despite the identification of multiple families of drug transporters in the human genome, including at least 48 sequences of putative proteins having characteristics of ABC-transporters, the functional characterization of these transporters is lacking.

The present invention describes the function of a protein, not of the ABC transporter family, that has a novel role as a primary active transporter of xenobiotics, their conjugates, toxic metabolic by-products (including drug- or physiologically-induced), and other chemicals (e.g., chemotherapeutic agents), especially those involved in drug resistance. The novel protein of the present invention functions as a Ral-binding, GTPase-activating protein or RalBP1. RalBP1 function results in transport of molecules associated with drug resistance and of exogenous and endogenous toxicants.

DNP-SG ATPase: A Transporter for Anionic and Cationic Xenobiotics

DNP-SG ATPase is a protein in membranes of human cells that catalyzes ATP hydrolysis in the presence of GSH-conjugates. It was so named because S-(2,4-dinitrophenyl)glutathione (DNP-SG) stimulated its ATPase activity. The presence of DNP-SG ATPase was demonstrated in all human tissues examined including liver, heart, lung, muscle, kidneys, erythrocytes, leukocytes and various human cell lines of diverse tissue origin. See LaBelle, et al., FEBS Lett. 228:53-56, 1988; Sharma, et al., Biochem. Biophys. Res. Commun. 171:155-161, 1990; Saxena, et al., Arch. Biochem. Biophys. 298:231-237, 1992; Awasthi, et al., J. Clin. Invest. 93:958-965, 1994; Awasthi, et al., Biochemistry 37:5231-5238, 1998a; Awasthi, et al., Biochemistry 37:5239-5248, 1998b; each incorporated herein by reference. DNP-SG ATPase-mediated ATP hydrolysis was stimulated not only by organic anions (e.g., DNP-SG), but by cations such as chemotherapeutic agents (e.g., doxorubicin or DOX) and their metabolites. DNP-SG ATPase catalyzed transport of anionic GSH conjugates as well as of weakly cationic drugs such as DOX and colchicine (Awasthi, et al., 1994, 1998a, 1998b, supra).

ATP-dependent transport of both anions and cations against a concentration gradient was demonstrated in proteoliposomes reconstituted with highly purified DNP-SG ATPase. Transport was temperature-dependent and sensitive to the osmolarity of the assay medium. ATP hydrolysis was required for the transport because when ATP was replaced by its non-hydrolyzable analogue, methylene-adenosine triphosphate (Met-ATP), transport activity was abolished. This suggested that transport was directly coupled to ATP hydrolysis, and that DNP-SG ATPase was a primary active transporter. Antibodies raised against DNP-SG ATPase inhibited the transport of anions and cations in inside-out vesicles (IOVs) prepared from erythrocyte membranes suggesting that the transport was specifically catalyzed by DNP-SG ATPase. On the other hand, antibodies against MRP1 or Pgp neither recognized DNP-SG ATPase in Western blots nor affected its transport activity, establishing that DNP-SG ATPase was a distinct transporter.

A protein related to DNP-SG ATPase was also identified in rodents (Zimniak, et al., Arch. Biochem. Biophys. 292:534-538, 1992; Zimniak and Awasthi, Hepatology 17:330-339, 1993; Pikula, et al., J. Biol. Chem. 269:27566-27573, 1994a; Pikula, et al., J. Biol. Chem. 269:27574-27579, 1994b; each incorporated herein by reference). Antibodies against human DNP-SG ATPase recognized the protein in rat canalicular membranes. When purified and reconstituted in proteoliposomes, it catalyzed concentrative transport of DNP-SG with kinetic parameters similar to those of human DNP-SG ATPase. The biochemical characteristics of the rat transporter and human DNP-SG ATPase were clearly distinct from the MRP2 from human and rats. These results clearly demonstrate that in mammals, other transporter(s) besides MRP2 is/are present.

Cloning of DNP-SG ATPase and its Identity with RalBP1

The molecular identity of DNP-SG ATPase remained elusive for over a decade because of the inherent difficulties in its purification (e.g., protein was prone to degradation, and peptides of varying chain lengths were observed in SDS gels of purified preparations, especially a 38 kDa peptide fragment). Purified preparations highly enriched in the 38 kDa peptide were found to mediate ATP-dependent, uphill transport of anions and cations in reconstituted proteoliposomes.

Immunoscreening of a human bone marrow cDNA library using polyclonal antibodies against the 38 kDa DNP-SG ATPase peptide yielded RalBP1 (Awasthi, et al., Biochemistry 39:9327-9334, 2000, incorporated herein by reference). At this time RLIP was thought of as a Ral binding, GTPase-activating protein (GAP), and to bridge the Ral, Rac, Cdc42 pathways.

The present disclosure now describes the expression of RalBP1 in E. coli that shows the recombinant protein readily undergoes degradation, yielding peptide fragments in SDS gel dependent on the conditions of purification, including a 95 kDa band and 38 kDa fragment. All the fragments are recognized by antibodies raised against DNP-SG ATPase and have internal sequences of RalBP1 (FIG. 2), demonstrating that these fragments originate from RalBP1 and result from proteolytic processing. Primary fragments are the C-RalBP1$^{410-654}$ and N-RalBP1$^{1-367}$ derived from the C- and N-terminus of RalBP1, respectively (Awasthi, et al., Biochemistry 40:4159-4168, 2001, incorporated herein by reference).

Figure 2:
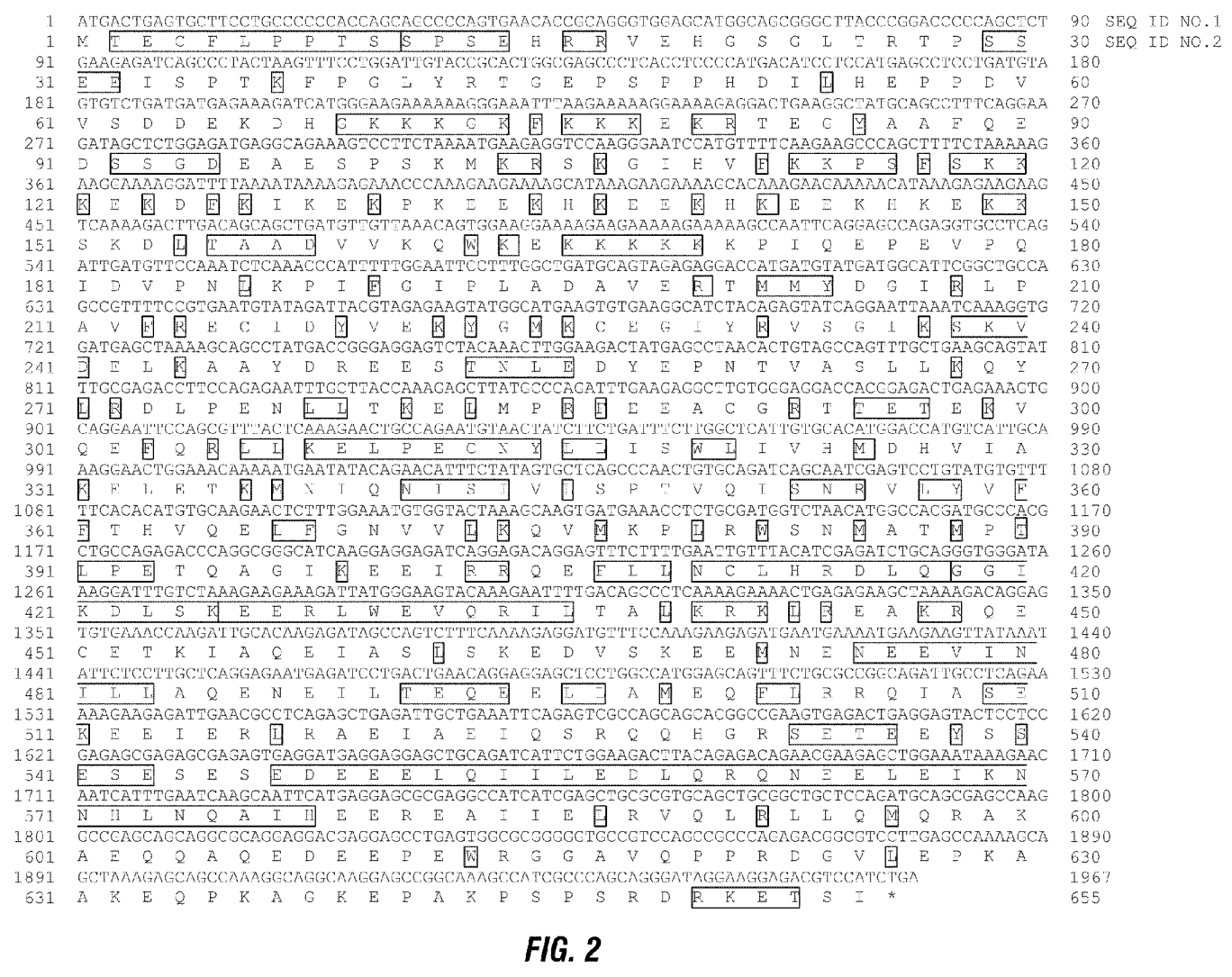

For FIG. 2, human bone marrow cDNA lambda gt11 expression library was screened with antibody against human DNP-SG ATPase, the positive plaques were purified and the recombinant lambda DNA were sequenced and sequence comparisons with published sequences were generated by the Blast Program available as a network service from the National Center for Biotechnology Information, NIH, such that the results showed the DNA sequence from the positive plaque was the same as the human RalBP1 protein mRNA coding sequence. The encoding sequence of RalBP1 was subcloned into prokaryotic expression vector pET30 and the recombinant RalBP1 was purified and sequenced and the deduced amino acid sequence was analyzed with the help of the Wisconsin Genetics Computer Group with different sequence identifications that include experimentally determined sequences of RalBP1 peptides obtained during purification (e.g., leucine zipper pattern, N-myristoylation site, trypsin cut site, chymotrypsin site, protein kinase C phosphorylation site, tyrosine kinase phosphorylation site, N-glycosylation site; cAMP-dependent protein kinase site, cGMP-dependent protein kinase site, and casein kinase II phosphorylation site).

RalBP1 Mediates ATP-Dependent Transport of Organic Anions and Cations

DNP-SG ATPase and RalBP1 may be, in many species, the same protein. Hence, recombinant RalBP1 (rec-RalBP1) shows constitutive ATPase activity stimulated by anionic (e.g., DNP-SG) and cationic (e.g., DOX) ligands with similar Km. Purified rec-RalBP1 reconstituted in proteoliposome (e.g., with asolectin or phospholipids of defined composition) catalyzes ATP dependent, uphill transport of anionic conjugates (e.g., DNP-SG, GS-HNE) and cationic amphiphilic drugs (e.g., DOX and daunomycin) such as those used in cancer chemotherapy. The results show that the mechanism through which RalBP1 transports charged chemicals (e.g., anthracyclines, vincristine) is distinct from that of MRP1. RalBP1 is not selective, it transposes both anions as well as cations. More importantly, the transport does not require GSH co-transport.

TABLE 1 summarizes structural characteristics, chromosomal location, tissue localization and substrate profiles of RalBP1, MRP1 and Pgp. TABLE 1 shows that RalBP1 does not share structural attributes with MRP1 or Pgp.

TABLE 1

Comparison of the characteristics of RLIP76 with Pgp (MDR1) and MRP1

|  | RalBP1 | MDR1 (Pgp) | MRP1 |
|---|---|---|---|
| Mol. Weight | 76 kDa | 170 kDa | 190 kDa |
| Chromosomal Location | Chromosome 18 | Chromosome 7 | Chromosome 16 |
| Topology | No clearly defined TMDs. One NBD each in the N and C-terminal domains are distinct from Walker A and B motifs. | 2 TMDs and 2 NBDs with Walker A and B motifs. | 2 TMDs similar to Pgp with an extra TMD0 connected with L0 loop. 2 NBDs with Walker A and B motifs. |
| Expression in human tissues | Ubiquitously expressed in mammalian tissue: erythrocytes, liver, lung, bone, muscle, kidney, and from cultured cells of mammalian origin. | Widely expressed in human tissue: liver, kidney, brain, pancreas, colon adrenal gland, small intestine. | Widely expressed in human tissue: epithelia, muscle cells and macrophages. |
| Localization in human tissues | Plasma membrane, nuclear membrane and cytoplasm. | Apical surface of epithelia (normal tissue); plasma membrane (malignant cells). | Cytoplasmic or unidentified vesicular fraction (normal); plasma membrane (malignant cells). |
| Transport allocrites (example of substrates) | Cations and anions; GSH-conjugates, glucuronides, vinca-alkaloids, anthracyclins; GSH not required for co-transport. | Vinca-alkaloids, anthracyclins, taxanes GSH not required for co-transport. | GSH-conjugates, glucuronides, bile salts; GSH co-transport required for vinca-alkaloids, anthracyclins. |

Abbreviations:
TMD = trans membrane domain;
NBD = nucleotide binding domain.

As described herein, physiologic significance of the ATP-dependent transport of both anions and cations by RalBP1 was confirmed by transfection experiments. Cells overexpressing RalBP1 show increased efflux of anions and cations (e.g., DOX, GS-HNE, leukotrienes) and acquired resistance to both DOX and 4-HNE induced cytotoxicity.

The transport of DOX is demonstrated in crude erythrocyte membrane vesicles. Addition of purified protein to crude erythrocyte membrane vesicles resulted in increased ATP-dependent DOX-transport in these vesicles in a manner linearly dependent on the amount of purified protein added. In these vesicles, DOX transport was competitively inhibited by anionic metabolites GS-E (DNP-SG), and bilirubin-ditaurate, as well as cationic drugs including anthracyclines (e.g., daunorubicin, mitoxantrone), vinca alkaloids (e.g., vinblastine), and calcium channel inhibitors (e.g., verapamil); see TABLE 2.

TABLE 2

Stimulation of human erythrocyte DNP-SG ATPase (RalBP1) activities

| Stimulator/Allocrite | Fold Activation | $K_M (\mu M)$ |
|---|---|---|
| Leukotriene C4 | 2.7 | 5.3 |
| Leukotriene D4 | 1.9 | 7.7 |
| Leukotriene E4 | 2.0 | 10 |
| N-acetyl Leukotriene E4 | 2.1 | 2.6 |
| Adriamycin | 2.3 | 2.8 |
| Dihydroadriamycin | 1.9 | 2 |
| Adriamycinone | 2.2 | 5.8 |
| Dihydroadriamycinone | 2.4 | 5.2 |
| Deoxyadriamycinone | 2.1 | 7.6 |
| S-(methyl)-glutathione | 1.4 | 137 |
| S-(n-propyl) glutathione | 1.5 | — |
| S-(n-pentyl) glutathione | 1.6 | — |
| S-(n-decyl) glutathione | 1.7 | 1528 |
| S-(p-chlorophenacyl) glutathione | 1.8 | — |
| S-(9,10-epoxy stearyl) glutathione | 1.9 | 674 |
| S-(p-nitrobenzyl) glutathione | 1.9 | — |
| S-(dinitrophenyl) glutathione | 2.0 | 58 |

ATPase activity of purified protein fractions was then measured in the absence and presence of several stimulators. Each assay was performed with 9 replicates and about. 2 μg protein was used for each determination. Km values were obtained from double reciprocal plots of stimulator vs. activity. For fold activations shown in TABLE 2, the concentration of stimulator used was generally 2-fold the Km. TABLE 2 explains the pharmacologic and toxicologic interactions between certain cationic drugs (e.g., natural product chemotherapy agents, calcium channel blockers, immune suppressants) and electrophilic compounds/drugs (e.g., alkylating chemotherapy agents, endogenously generated electrophiles from lipid oxidation) that may be metabolized to their by-products such as GS-E. This is particularly useful because some cells (e.g., erythrocytes) do not possess the full complement of metabolic machinery to metabolize GS-E to mercapturic acids.

Structure of RalBP1

Primary structure of RalBP1 reveals several interesting features. The protein may be divided into four regions out of which two central domains carry a Rac1/CDC42 GAP activity and a Ral binding domain. The function of two flanking domains are still unknown. The amino acid sequence of RalBP1 is depicted in FIG. 2 and indicates the presence of sites for N-glycosylation (amino acid ("aa") 341-344), cAMP (aa 113-116), cGMP-dependent protein kinase phosphorylation (aa 650-653), tyrosine kinase phosphorylation (aa 308-315), N-mysristolation (aa 21-26, aa 40-45, aa 191-196), leucine zipper pattern (aa 547-578) and several protein kinase C phosphorylation, casein kinase II phosphorylation, trypsin and chemotrypsin cut sites. The presence of such motifs in the primary structure of RalBP1, and its facile proteolytic degradation shows RalBP1 to be involved in several intra and extracellular processes (e.g., protein processing, intracellular signaling, protein degradation, recognition, tagging, etc.) and that proteolytic processing of RalBP1 is required for the multiple functions. The peptide fragments of RalBP1 individually or in association with other fragments may catalyze these various functions. For example, N-terminal and C-terminal fragments of RalBP1, fragments that are individually incapable of mediating ATP-dependent transport, can catalyze the transport of electrically charged drugs (e.g., DOX, colchicines) when reconstituted together in proteoliposomes.

RalBP1 Contains Two ATP-Binding Sites

RalBP1 expressed in cultured cells or in $E.\ coli$ undergoes facile proteolysis during purification. Two most prominent peptides, N-RalBP1$^{1-367}$ and C-RalBP1$^{410-655}$, arising from the N- and C-termini of RalBP1, respectively, appear as 49 kDa and 38 kDa in SDS-gels. Both these peptides display constitutive ATPase activity that may be stimulated in the presence of the anionic or cationic ligands transported by RalBP1. Both peptides bind ATP, as shown by photoaffinity labeling that increased in the presence of vanadate, indicating the trapping of a reaction intermediate in the ATP binding site. None of the two fragments catalyze transport when reconstituted alone in proteoliposomes. However, when reconstituted together, ATP-dependent transport of charged chemicals (e.g., DNP-SG, DOX) is observed with kinetic parameters similar to those for RalBP1. The ATP binding sites in N-RalBP1$^{1-367}$ and C-RalBP1$^{410-655}$ were identified to be $^{69}$GKKKGK$^{74}$ and $^{418}$GGIKDLSK$^{425}$, respectively. Mutations of K$^{74}$ and K$^{425}$ in the N- and C-terminal peptides, respectively, abrogate the ATPase activity, ATP binding capacity and transport function. The sequence of these ATP binding sites are not identical to the consensus sequence for the P-loop (Walker motif).

Unlike the ABC transporters, no transmembrane alpha-helices are evident in the RalBP1 sequence. Its association with membranes has, however, been demonstrated by immuno-histochemical studies using specific antibodies (Awasthi, et al., *Proc. Am. Assoc. Cancer Res.* 43:Abst. 4717, 2002; incorporated herein by reference). The extraction of RalBP1 from cell lysates requires detergent, suggesting membrane association, a feature essential for transport.

These findings show a greater diversity in this transporter, in terms of structural elements defining ATP binding and mode of membrane insertion, than is currently accepted. In addition, the distinction between transporters for anions as opposed to neutral or cationic substrates is blunted because RalBP1 catalyzes the transport of both, and, in contrast to MRP 1, does so without co-transporting GSH.

Another intriguing aspect of RalBP1 function is that it undergoes facile proteolytic fragmentation and many of the resulting peptides may be reconstituted into an active transport complex, a function that may help regulate exocytosis and membrane ruffling. Toxic Compounds and Xenobiotic Protection with RalBP1

Figure 3:
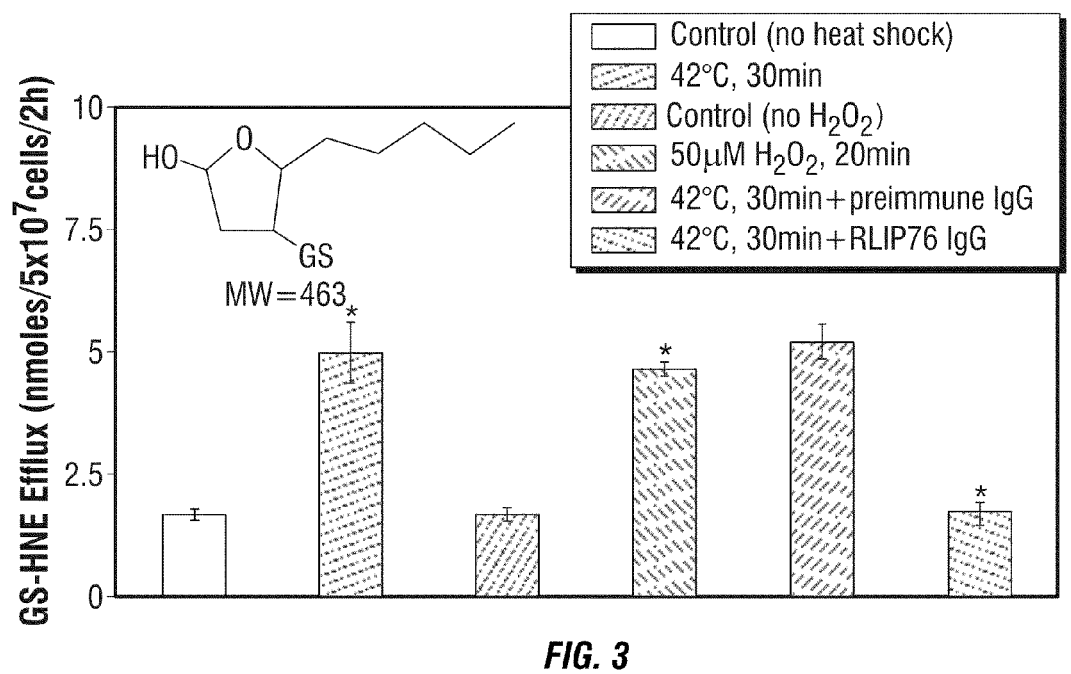
FIG. 3 depicts the effect of heat shock and $H_2O_2$ exposure on GS-HNE transport in K562 cells.

Physiologic stress or damage (e.g., mild transient heat shock or oxidative stress) induces RalBP1 activity and the activity is in advance of inducing other heat shock proteins or the antioxidant enzymes, which constitute the typical stress response (Cheng, et al., *J. Biol. Chem.* 276:41213-41223, 2001, incorporated herein by reference). For example, when K562 cells are exposed to a mild heat shock (about 42° C. for 30 minutes) or oxidative stress (about 50 μM $H_2O_2$ for 20 minutes) and allowed to recover for 2 hours, enhanced LPO is observed in stressed cells as compared to non-stressed cells. There is a 3-fold induction of a GST isozyme, hGST5.8, that catalyzes the conjugation of 4-HNE and GSH to GS-HNE, and a 3.7-fold induction of RalBP1 that mediates ATP-dependent transport of GS-HNE from cells. As shown in FIG. 3, the cells preconditioned with stress transported GS-HNE at three-fold higher rate as compared to unstressed cells. This followed a greater than 3-fold induction of RalBP1 in the preconditioned cells. For FIG. 3, K562 cells (5×10$^7$ cells) were exposed to 42° C. for 30 minutes, and allowed to recover for 2 hours in medium at 37° C. Cells were pelleted and re-incubated for 10 minutes at 37° C. in 2 mL medium containing 20 μM [$^3$H]-4-HNE, followed by pelleting and two washes with 2 mL of phosphate-buffered saline (PBS). The supernatants and washings were discarded and the cells were incubated at 37° C. for 2 hours in 2 mL of 4-HNE free medium after which radioactivity was determined in the medium. The hemiacetal 3-(4-hydroxynonanyl)glutathione (inset, FIG. 2) was isolated by HPLC and characterized by mass spectral analysis. For $H_2O_2$ treatment the cells were incubated for 20 minutes at 37° C. in media containing 50 μM $H_2O_2$ and after incubation, the cells were pelleted, washed free of $H_2O_2$, incubated in $H_2O_2$ free medium at 37° C. for 2 hours and subsequently the radioactivity was measured in the medium. For treatment with antibodies, the cells, after heat shock treatment, were allowed to recover for 1 hour and respective IgGs were added (20 μg/mL medium) and incubated at 37° C. for additional 1 hour, such that the cells were pelleted and [$^3$H] GS-HNE transport was measured as described above. The values in FIG. 3 are shown as mean±S.D. (n=3 separate experiments) and * indicates statistically significant differences between treated and control cells evaluated by the Student's t test (P<0.05).

To confirm that RalBP1 does indeed transport the GS-HFNE and not its degradation products or metabolites, the transported allocrite, hemiacetal of 3-(4-hydroxynonanyl) glutathione, was isolated from media and characterized by mass spectral analysis.

Figure 4A:
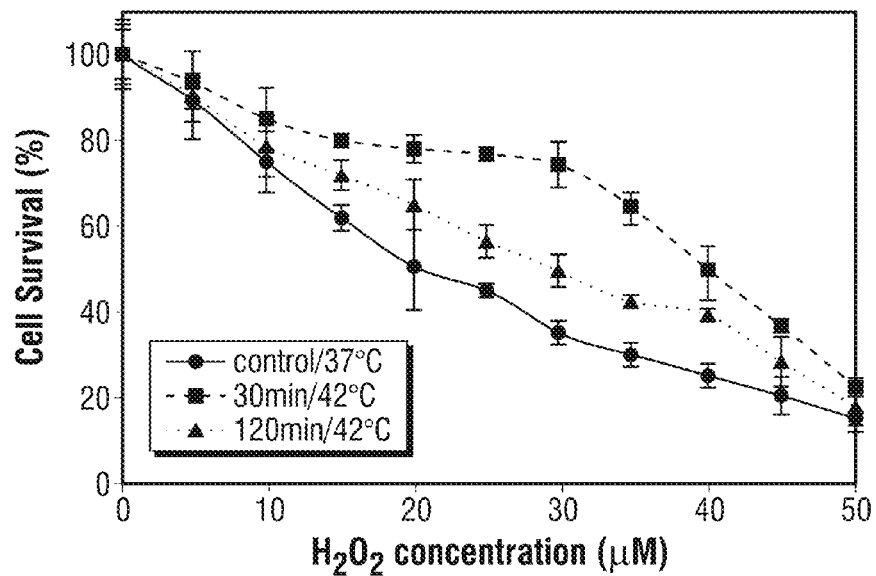
FIG. 4A depicts the effect of heat shock on the $H_2O_2$ mediated cytotoxicity in K562 cells and FIG. 4B depicts the protective effect of heat shock and $H_2O_2$ pre-treatment on $H_2O_2$ induced apoptosis in K562 cells.
Figure 4B:
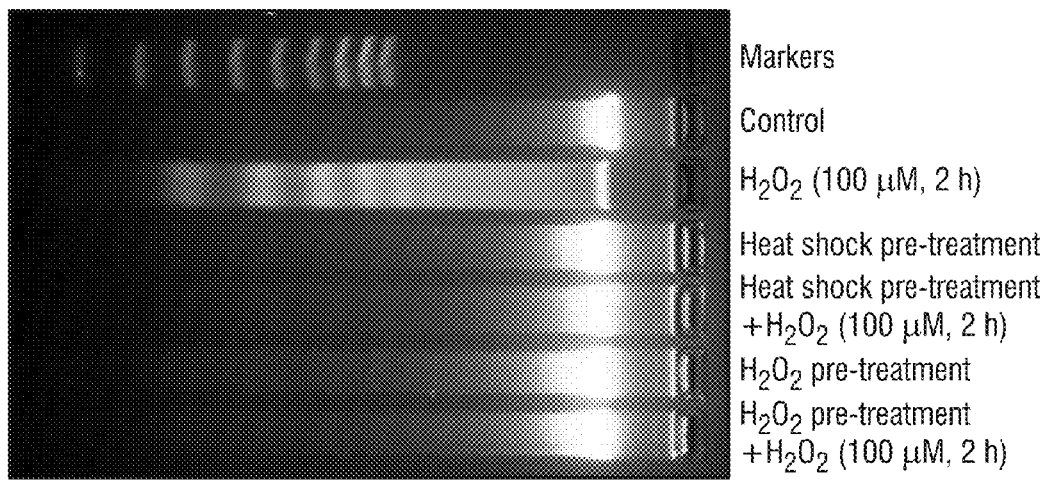

Increased efflux of GS-HNE was blocked by coating the cells with antibodies against RalBP1, confirming that GS-HNE was transported by RalBP1. More importantly, stress pre-conditioned cells with induced hGST5.8 and RalBP1 acquired resistance to $H_2O_2$-mediated cytotoxicity (FIG. 4A) and to apoptosis by (FIG. 4B) suppressing a sustained activation of c-Jun N-terminal kinase and caspase 3. For FIG. 4A, aliquots (about 40 μL) containing 2×10$^4$ control or heat shock treated cells were washed with PBS and plated into 8 replicate wells in a 96-well plate, wherein $H_2O_2$ (about 50 μM) in 10 μL of PBS was added and the plates were incubated at 37° C. for 2 hours, after which about 200 μL of growth medium was added to each well. Following 72 hours of incubation at 37° C., the MITT assay was performed and the OD$_{590}$ values of sample subtracted from those of respective blanks (no cells) were normalized with control values (no $H_2O_2$). Averages and standard deviations from three separate determinations of cytotoxicity of 4-HNE and $H_2O_2$ are shown in FIG. 4A. For FIG. 4B, 2.5×10$^6$ K562 cells in 5 mL medium were treated with heat shock at 42° C. for 30 minutes, or 50 μM $H_2O_2$ (final concentration in medium) for 20 minutes and allowed to recover for about 2 hours in normal growth medium at 37° C. The cells, pre-conditioned with heat shock or $H_2O_2$ treatment, were treated with heat for 2 hours and 100 μM $H_2O_2$ for 2 hours. DNA (about 1 μg) extracted from the cells was electrophoresed on 2% agarose gels containing 10 μg/mL ethidium bromide; lanes representing different treatments are marked.

The protective effect of stress pre-conditioning against $H_2O_2$ or 4-HNE induced apoptosis was abrogated by coating the cells with anti-RalBP1 IgG, which inhibited the efflux of GS-HNE from cells (FIG. 5). For FIG. 5, aliquots (about 50-100 μL) containing $1-2 \times 10^6$ cells were fixed onto poly-L-lysine-coated slides by cytospin at 500×g for 5 minutes and the TUNEL apoptosis assay was performed. Slides were analyzed by fluorescence microscope using a standard fluorescein filter and photomicrographs at 400× magnification are presented. Apoptotic cells showed characteristic green fluorescence. FIG. 5 includes the following: Panel 1, control cells, without heat shock pre-treatment, incubated with 20 μM 4-HNE for 2 hours; Panel 2, control K562 cells pre-treated with heat shock (42° C., 30 minutes) and allowed to recover for 2 hours at 37° C.; Panel 3, cell pretreated with heat shock, allowed to recover for 2 hours at 37° C. followed by incubation in medium containing 20 μM 4-HNE for 2 hours at 37° C.; Panel 4, heat shock pre-treated cells, allowed to recover for 1 hour at 37° C., anti-RalBP1 IgG was added to medium (20 μg/mL final concentration) and incubated for an additional 1 hour and cells were then incubated for 2 hour at 37° C. in medium containing 20 μM 4-HNE.

Induction of hGST5.8 and RalBP1 by mild, transient stress and the resulting resistance of stress-pre-conditioned cell to apoptosis is a general phenomenon, because it is not limited to K562 cells, but is evident in other cells (e.g., lung cancer cells, H69, H226, human leukemia cells, HL60, human retinal pigmented epithelial cells). Hence, transport activity of RalBP1 regulates the intracellular levels of potential toxic by-products. Examples of toxic by-products are the lipid peroxidation products involved in apoptosis signaling, differentiation, and cell proliferation.

Radiation Protection with RalBP1

Figure 6:
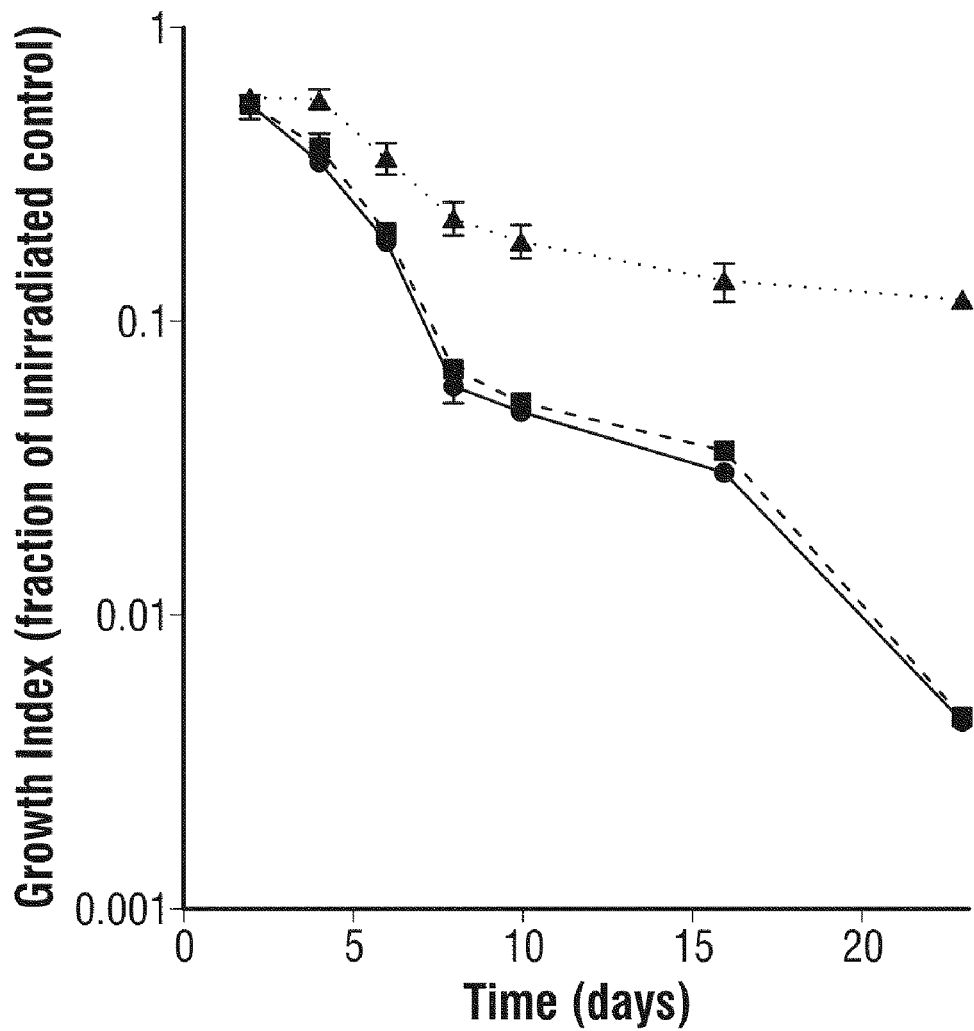
FIG. 6 depicts the effect of RalBP1 on radiation sensitivity, wherein the mean and standard deviation of values from three groups shown are: without treatment with liposomes (circle), treatment with liposomes without RalBP1 (square), and treatment with liposomes with RalBP1 (triangle).

The protective effects of RalBP1 goes beyond its protection of potentially toxic chemical substituents and their by-products. RalBP1-enriched cells are also resistant to toxicity from radiation. For example, as shown in FIG. 6, cells enriched with RalBP1 are remarkably resistant to radiation as compared to non-enriched control cells. Here, small cell lung cancer cells (H82) were loaded with RalBP1 by incubating with RalBP1 encapsulated in artificial liposomes. They were irradiated at 500 cGy with high-energy photon (6×10 volt photon/min) for 1.25 minutes. Cells were serially passaged daily by inoculating $0.5 \times 10^7$ trypan blue dye excluding cells/mL in fresh RPMI medium. For analysis, the cell density measured each day was normalized to cell density in respective non-irradiated controls.

As such, electrophilic products of lipid peroxidase (LPO) caused by reactive oxygen species generated during radiation may partly account for cell killings by radiation. Clearly RalBP1-mediated transport of GSH-conjugates of these electrophiles provides protection from radiation. Such protection may be readily transferred to a larger scale to protect mammals against damaging radiation, including ionizing, electromagnetic, thermal, and laser, wherein either long- or short-range electrons are involved.

Figure 7:
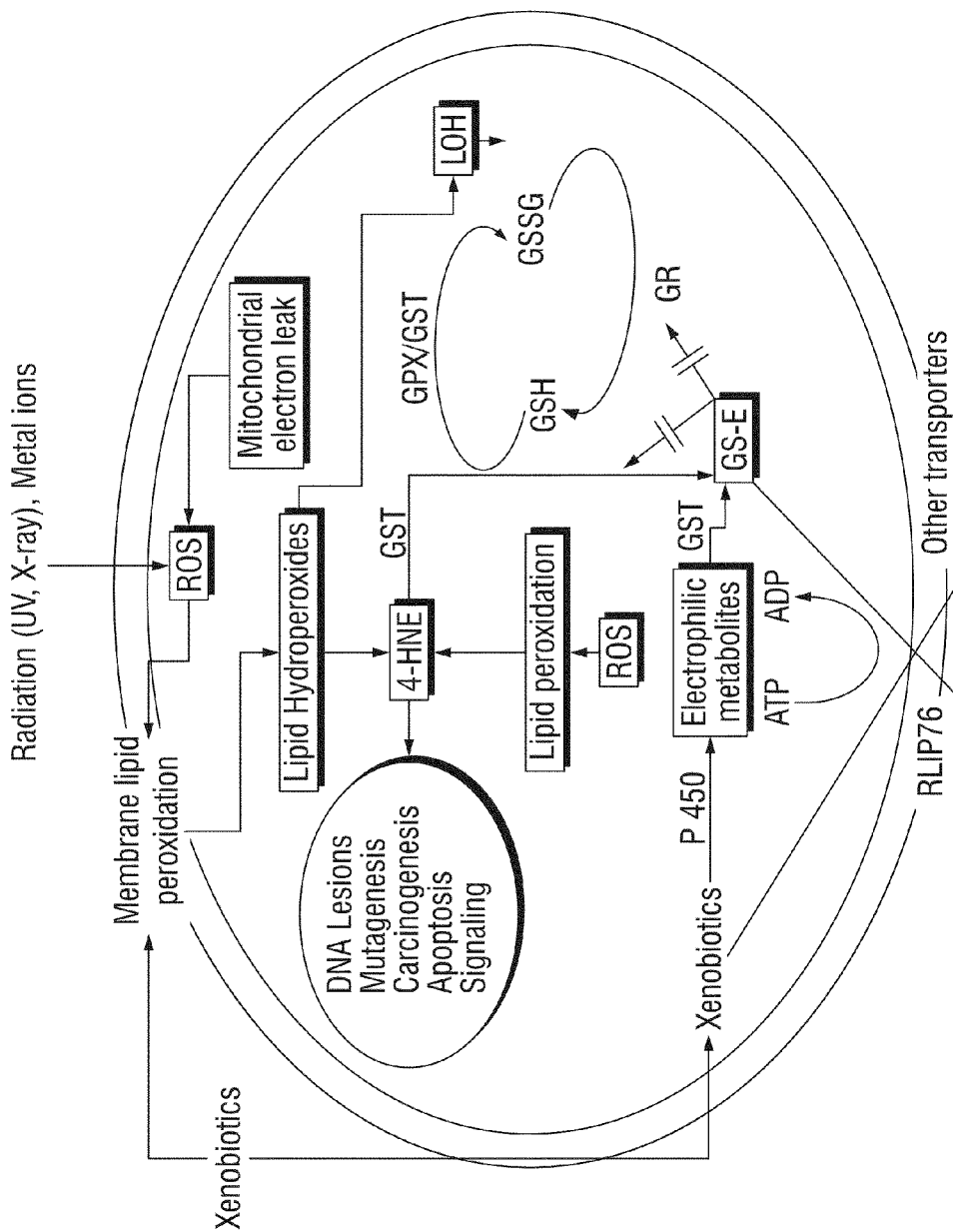
FIG. 7 depicts examples of the physiological significance of RalBP1.

Therefore, RalBP1 mediates transport of endogenously generated chemicals, metabolic products, their by-products and exogenously administered drugs or radiation, and their by-products. RalBP1 mediates the transport of most chemicals and by-products that also involve GS-E (e.g., conjugate of 4-HNE). For example, RalBP1-enriched cells are resistant to toxicity in the form of chemical toxicity (organic or inorganic) or from damage (e.g., from stress, oxidation, alkylation, radiation). The function of RalBP1 via an ATP-dependent efflux of xenobiotics (e.g., GS-E and exogenous and endogenous electrophiles) is shown in FIG. 7. Here, xenobiotics, radiation, their metabolites, mitochondrial electron transport and metal ions generate reactive oxygen species (ROS) that can cause membrane lipid peroxidation and 4-hydroxynonenal (the toxic end product of lipid peroxidation) cause DNA damage leading to mutagenesis, carcinogenesis and apoptosis as well as modulates the stress mediated signaling pathways. Clearly, RalBP1 mediates the ATP-dependent efflux of a wide variety of metabolic, stress, and pharmaceutical by-products, such as amphiphilic drugs, GSH-conjugates (GS-E) of both xeno- and endo-biotics, GS-HNE and leukotrienes, from eukaryotic cells. The transport of GS-E is crucial for maintaining functionality of GSTs and glutathione reductase (GR), because these enzymes are inhibited by GS-E. RalBP1 regulates the intracellular concentrations of 4-HNE by a coordinated mechanism with cellular GSTs.

RalBP1 and Multi-Drug Resistance

RalBP1 is also involved in the mechanism of multidrug resistance of cancer cells. RalBP1 mediates ATP-dependent primary active transport of not only anionic compounds (e.g., GSH-conjugates), but also the cationic chemotherapeutic drugs such as DOX, daunomycin and colchicine. The protein sequence of RalBP1 is not homologous to ABC-transporters, the proteins thought to be involved in the mechanisms of multi-drug resistance. RalBP1: (1) lacks any close homologs in humans; (2) displays ubiquitous expression in tissues; (3) lacks the classic nucleotide binding Walker domains; (4) has integral membrane association without clearly defined transmembrane domains; and most importantly, (5) has distinct functions not present in other transporters (e.g., has a role as a direct link to Ras/Ral/Rho and EGF-R signaling through its multifunctional nature including GAP-activity and Ras/Ral/Rho-regulated effector function involved in receptor mediated endocytosis). Its multifunctional nature is likely due to the presence of multiple motifs including Rho/Rac-GAP-domain, Ral-effector domain binding motif, two distinct ATP-binding domains, $H^+$-ATPase domain, PKC and tyrosine kinase phosphorylation sites, and its proteolytic processing into multiple smaller peptides that participate as components of macromolecular functional complexes.

RalBP1 overexpression confers resistance to both DOX and alkylating toxins such as 4-FINE by increasing their efflux from cells. RalBP1 can also modulate stress signaling by regulating intracellular concentrations of 4-HNE, as it is involved in stress signaling. Antibodies against RalBP1 can block the transport of drugs and enhance cytotoxicity of these drugs (e.g., chemotherapeutic agents) to cancer cells. The higher resistance to DOX of non-small cell lung cancer (NSCLC) cells as compared to the small cell lung cancer (SCLC) cells correlates with a higher RalBP1-mediated efflux of DOX in NSCLC (Awasthi, et al., In "Pharmacology and Therapeutics in the New Millenium" (Gupta, S. K., ed., pp. 713-725, Narosa Publishing House, New-Delhi, India, 2001), incorporated herein by reference). Coating with RalBP1 antibodies sensitizes NSCLC to DOX by blocking their RalBP1 mediated transport. Taken together, the present disclosure demonstrates that RalBP1 modulates drug sensitivity of cancer cells. RalBP1 is expressed in all human tissues and cell lines examined so far, and it catalyzes the transmembrane movement of physiologically relevant ligands as well as a wide variety of xenobiotics irrespective of their net charge.

The significance of RalBP1-mediated transport to the mechanisms of multidrug resistance may go beyond the protection of cells through drug efflux. RalBP1 also impacts on signaling mechanisms via the modulation of the intracellular concentration of GS-HNE and its precursor, 4-HNE, which is known to cause cell cycle arrest and promote differentiation and apoptosis in cancer cell lines (Cheng, et al., *Arch. Biochem. Biophys*. 372:29-36, 1999; incorporated herein by reference). In addition, the effects of 4-HNE on cell cycle signaling may be concentration dependent as it can have the opposite effect at lower concentrations where proliferation is observed in the presence of low 4-HNE levels. The level of 4-HNE reflects the stress status of the cell, and to convey the corresponding signal to the cell cycle and/or apoptosis machinery. Induction of RalBP1, by damage, oxidative or chemical stress (e.g., due to anticancer drugs), depletes 4-HNE and thus promotes the proliferation of cancer cells.

RalBP1, therefore has a two-pronged effect in multi-drug resistance; in addition to xenobiotic and other potentially toxic chemical or drug transport, RalBP1 shifts the signaling balance in favor of cell proliferation.

RalBP1 and Radiation Sensitivity Using Knockout Mice

As described, RalBP1 (also referred to as RALBP1 or Ral-binding protein) is a glutathione-conjugate transporter that is a critical component of stress-response in cultured cells and provides protection from stressors including heat, oxidant chemicals, chemotherapeutic agents, UV irradiation and X-irradiation.

Figure 8:
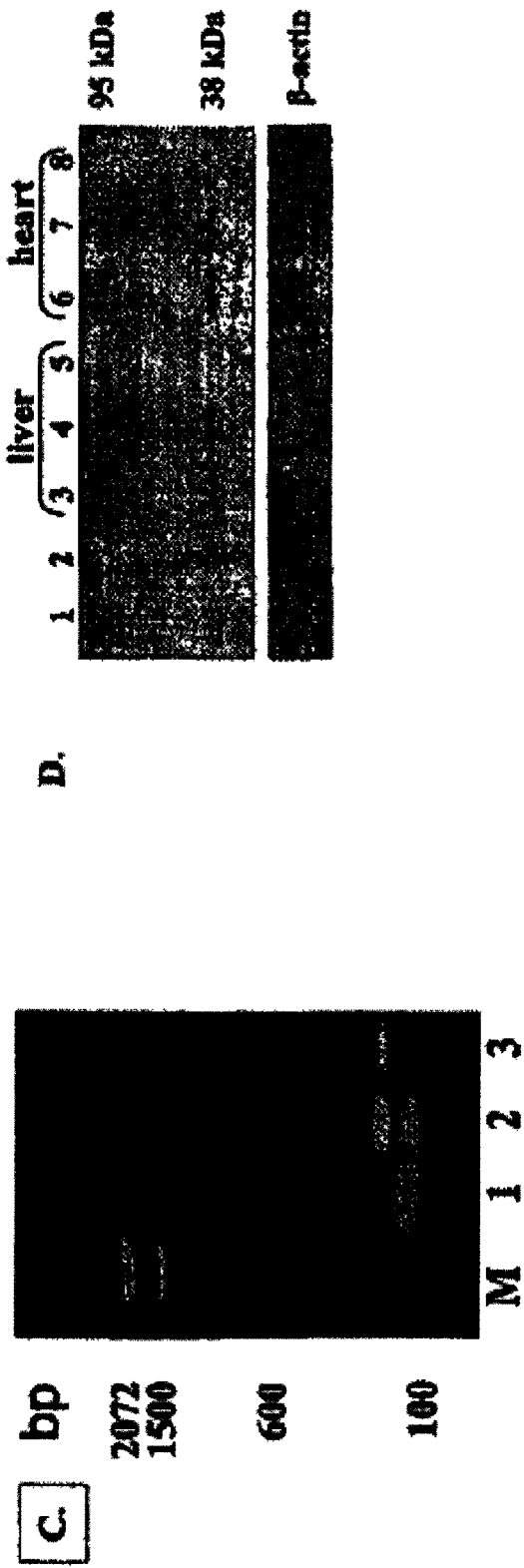
FIG. 8 depicts the knockout and genotyping strategy as embodied in one aspect of the present invention.

C57B mice which carry heterozygous (+/−) or homozygous (−/−) deletion of the RIP1 gene (mouse version of RalBP1) were created. These mice were created using Cre-Lox technology that can selectively suppress genes (FIG. 8A and FIG. 8B). From RIP1+/− animals, obtained from Lexicon Genetics (The Woodlands, Tex.), colonies of RIP1+/+, RIP1+/−, and RIP1−/− C57B mice were established by segregation and mating of animals based on genotyping by polymerase chain reaction (PCR) on tail tissue (FIG. 8C). Western-blot analysis of mouse tissues using anti RalBP1 antibodies confirmed decreased RIP1 levels in the RIP1+/− mouse, and its absence in tissues from the RIP1−/− mouse (FIG. 8D).

For FIG. 8A, the knockout and genotyping strategy is the following. The sequence around the insertion site with the up-stream (SEQ ID NO: 3) and down-stream (SEQ ID NO: 4) PCR primers (in bold-underline) are shown. The third primer was an LTR primer (SEQ ID NO: 5 in FIG. 8B). About ten weeks old C57 mice born of heterozygous x heterozygous mating were genotyped by PCR strategy, in which mouse tail DNA was isolated and used as a template in PCR reaction. A sample genotyping result is given. When all three primers are used in PCR, DNA from wild-type animal should yield a 200 bp band, knockout homozygous animal should yield a 150 bp band, and knockout heterozygous animal should yield both bands. In FIG. 8C, lane M is DNA ladder, lanes 1, 2 and 3 are from homozygous knockout, heterozygous knockout and wild-type animals. FIG. 8D shows analysis of RalBP1 protein in tissues from wild-type and RalBP1 knockout mice by Western blot. Crude membrane fractions from several tissues were prepared and subjected to SDS-PAGE with application of 100 µg protein per lane. Gels were transblotted on to nitrocellulose membranes, followed by Western blotting using anti-RalBP1 IgG as primary antibody. The blots were developed with 4-chloro-1-naphthol as chromogenic substrate. Lane 1 contained detergent extract of bacterial membranes from rec-£. coli expressing RalBP1 (pET-30a[+]-RLQLIP-BL21 (DE3)−). Lane 2 was blank. Lanes 3-5 contained membrane extract from liver and lanes 6-8 from heart. Lanes 3 and 6 contained protein from wild-type animal, lanes 4 and 7 contained protein from heterozygous RalBP1 knockout animal, and lane 5 and 8 contained protein from homozygous RalBP1 knockout animals (FIG. 8D). β-actin expression was used as internal control.

The present invention shows that loss of RalBP1 (shown as a RIP1 knockout) will confer sensitivity to X-irradiation, radiation sensitivity of RIP1−/− mice was compared with the RIP1+/+ by administering 500 cGy whole-body X-irradiation using a Varian Clinac Linear accelerator (2100C), followed by monitoring for survival. A representative experiment (FIG. 9A) shows a dramatic 11 day difference in median survival between RIP1−/− (0/6 surviving by day 13) as compared with RIP+/+ (2/6 surviving at day 28). These findings provide dramatic evidence for the radiation sensitivity conferred by loss of RIP1. For FIG. 9A, C57 RIP1+/+ (square) and −/− mice (diamond) were treated with 500 cGy total body X-irradiation and survival was monitored. Each group had 6 animals. Western blot analyses of RIP1−/− mouse tissues were performed after i.p. injection of RalBP1-liposomes (FIG. 9B and FIG. 9C). In the upper panel (FIG. 9B), RIP1−/− mice were treated with RalBP1-liposomes containing 200 µg RalBP1 protein i.p. and sacrificed 48 hours later. In the lower panel (FIG. 9C), RALBP1−/− mice were treated with 3 doses of 200 µg RalBP1 liposomes at time 0, 72 hours, and 120 hours, followed by sacrifice at 168 hours. Lanes labeled C are from mice treated with control liposomes without RalBP1 and R denotes mice treated with RalBP1-liposome. Tissues as indicated in FIG. 9B and FIG. 9C were homogenized and aliquots of the detergent solubilized crude membrane fraction containing 200 µg protein was subjected to SDS-PAGE, transblotted to nitrocellulose membrane using anti-RalBP1 as primary antibody and peroxidase-conjugated goat-anti-rabbit IgG as secondary antibody. The blots were developed with 4-chloro-1-naphthol. β-actin expression was used as loading control. RalBP1−/− mice treated with either control liposomes (square) or RalBP1-liposomes (diamond) at day −3, day +3 and day +5 of 500 cGy total body irradiation. Survival was monitored (FIG. 9D).

If loss of RIP1 was the major determining factor in this acquired radiation sensitivity, replacement of this deficit should reverse radiation resistance. Therefore, a liposomal delivery system for providing recombinant human RalBP1 to the tissues of knockout animals is presented. Methods for expressing recombinant human RalBP1 in *E. coli* and purifying the expressed protein to a high purity, >96% by amino acid composition analysis, and reconstituting its transport function in artificial liposomes are those commonly used by one of ordinary skill in the art (Awasthi, et al., 2000, supra). Liposomes were prepared in sufficient quantities and administered via the intraperitoneal (i.p.) injection to RIP1−/− animals.

Figure 9:
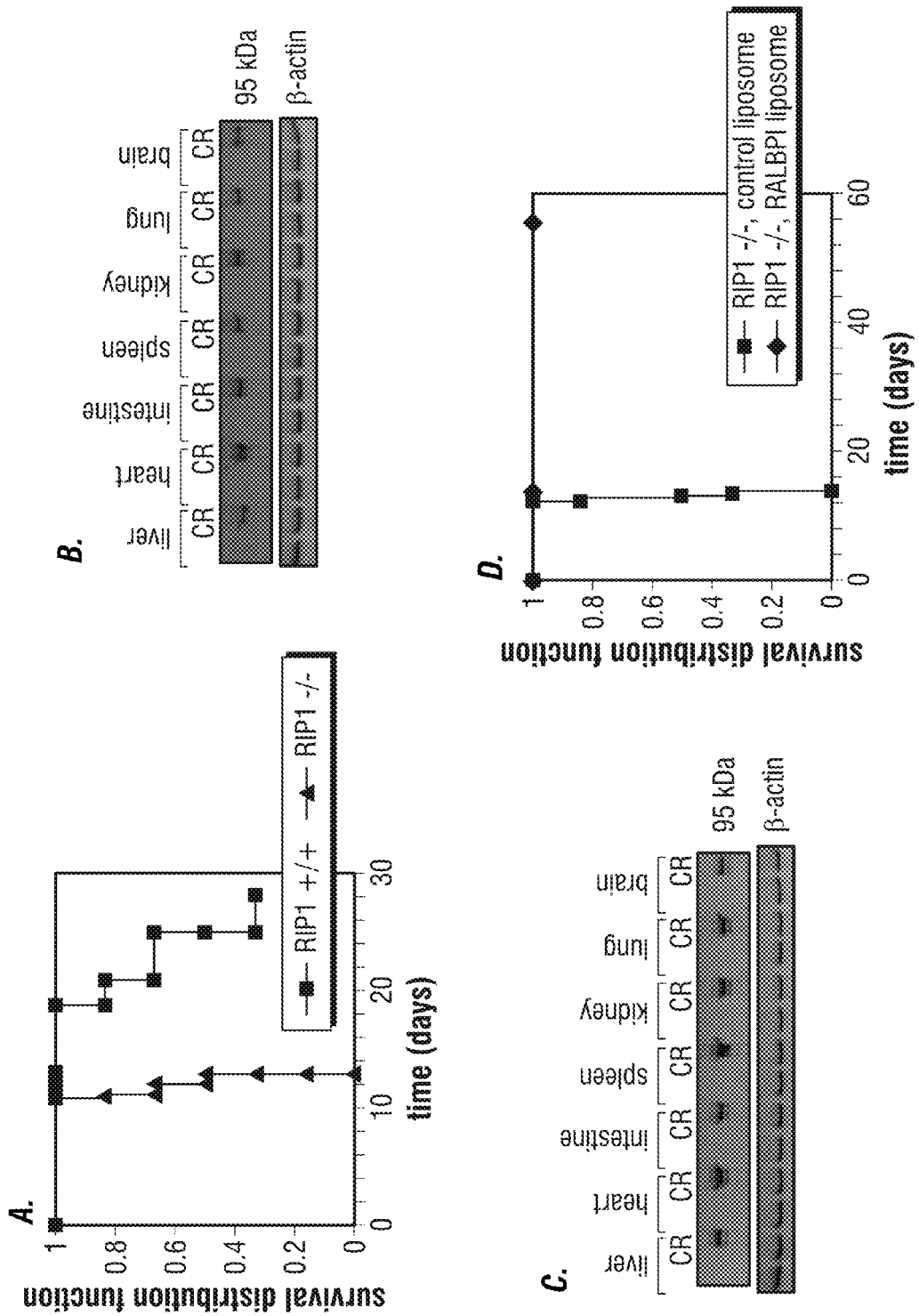
FIG. 9 depicts the effect of RIP1 on radiation sensitivity in male C57 mouse as embodied in one aspect of the present invention.

A single dose of RalBP1-liposomes containing 200 µg purified RalBP1 administered i.p. followed 48 hours later by sacrificing the animals and analyzing tissues immunologically for presence of RalBP1 showed convincingly that these liposomes could be used to deliver RalBP1 to all tissues of RIP1−/− mice (FIG. 9B). Administration of 3 doses of RalBP1-liposomes at the same dose over 8 days followed by sacrifice at day 10 showed further accumulation of RalBP1 in the RIP1−/− mouse tissues (FIG. 9C).

These Western-blot analyses confirmed the lack of any detectable RIP1 in any tissue from the −/− mouse and presence of a band at the expected Mr of 95 kDa for intact RalBP1 in all tissues examined from mice treated with RalBP1 liposomes. The 38 kDa band represents a C-terminal proteolytic fragment of RalBP1 beginning at aa 424. Remarkably, even the brain tissue took up a significant amount of RalBP1, a finding that may have significant pharmacological implications for delivery of drugs to the brain or other organs. The RalBP1 liposomes may incorporate one or more genes and targeted markers in order to deliver the gene to the targeted organ(s) of a mammal.

Delivery of RalBP1 to mouse tissues also results in reversal of radiation sensitivity. The example used to show this is with 12 male RIP1−/− mice randomized into two groups of 6, the first group receiving control liposomes containing no RalBP1, and the second group receiving RalBP1-liposomes administered by i.p. injection. Animals were subjected to 500-cGy whole-body X-irradiation and followed for survival. A dramatic difference is survival was observed with all 6/6 RalBP1-liposome treated animals surviving over 300 days, as compared with 0/6 control-liposome treated animals surviving by 13 days post irradiation (FIG. 9D). Remarkably, the RIP1−/− mice supplemented with RalBP1 had significantly improved survival as compared with even the RIP1+/+ mice. These findings conclusively demonstrate the radiation protective effects of RalBP1.

The mechanism for this radioprotective effect of RALBP1 was investigated in transport studies looking at the effect of RIP1 genomic deletion on GS-E transport capacity, oxidative-stress, and glutathione-linked antioxidant enzymes in animals without or with radiation. For transport studies, crude membrane inside-out vesicles (IOVs) from different tissues were used. The reaction mixture consisted of IOVs protein, 10 mM Tris-HCl, pH 7.4, 250 mM sucrose, 4 mM $MgCl_2$ and either 4 mM ATP or an equimolar concentration of NaCl. To start the reaction, appropriate volume of radiolabeled $^{14}C$-DOX or $^{3}H$-DNP-SG was added. The uptake was stopped by rapid filtration of the reaction mixture through 96 well nitrocellulose plate (0.45 μm pore size). After filtration, the bottoms of the nitrocellulose membranes were blotted dry with filter paper and punched out, and the associated radioactivity was measured by placing in liquid scintillation fluid. ATP-dependent uptake of either $^{14}C$-DOX or $^{3}H$-DNP-SG was determined by subtracting the radioactivity of the control without ATP from that of the experimental containing ATP and the transport of DOX or DNP-SG was calculated in terms of pmoles/min/mg IOV protein. GSH levels and enzyme activities for GST, GPX, GR, G6PD and γGCS activities were determined in 28,000×g supernatants of 10% homogenate, and LOON and TBARS were determined in whole crude homogenates using well established methods known to those of ordinary skill in the art.

Radioprotection

The example used to show the radioprotective effect is a study with a 2×2×3 factorial design (radiation x gender x genotype) and three animals per group. Six groups of irradiated animals were treated with 500 cGy whole body X-irradiation, and a remaining six groups were un-irradiated. Animals were sacrificed and autopsied at day 8 after irradiation. Seven tissues (brain, heart, lung, liver, kidney, intestine and spleen) were examined for content of parameters of oxidative injury and glutathione-linked enzymes. GS-E and DOX transport was examined in crude membrane vesicles prepared from plasma membrane fraction of heart tissues. Data was analyzed by ANOVA with one-way, two-way and three-way interactions between the three variables (gender, genotype, radiation) being compared.

Figure 10:
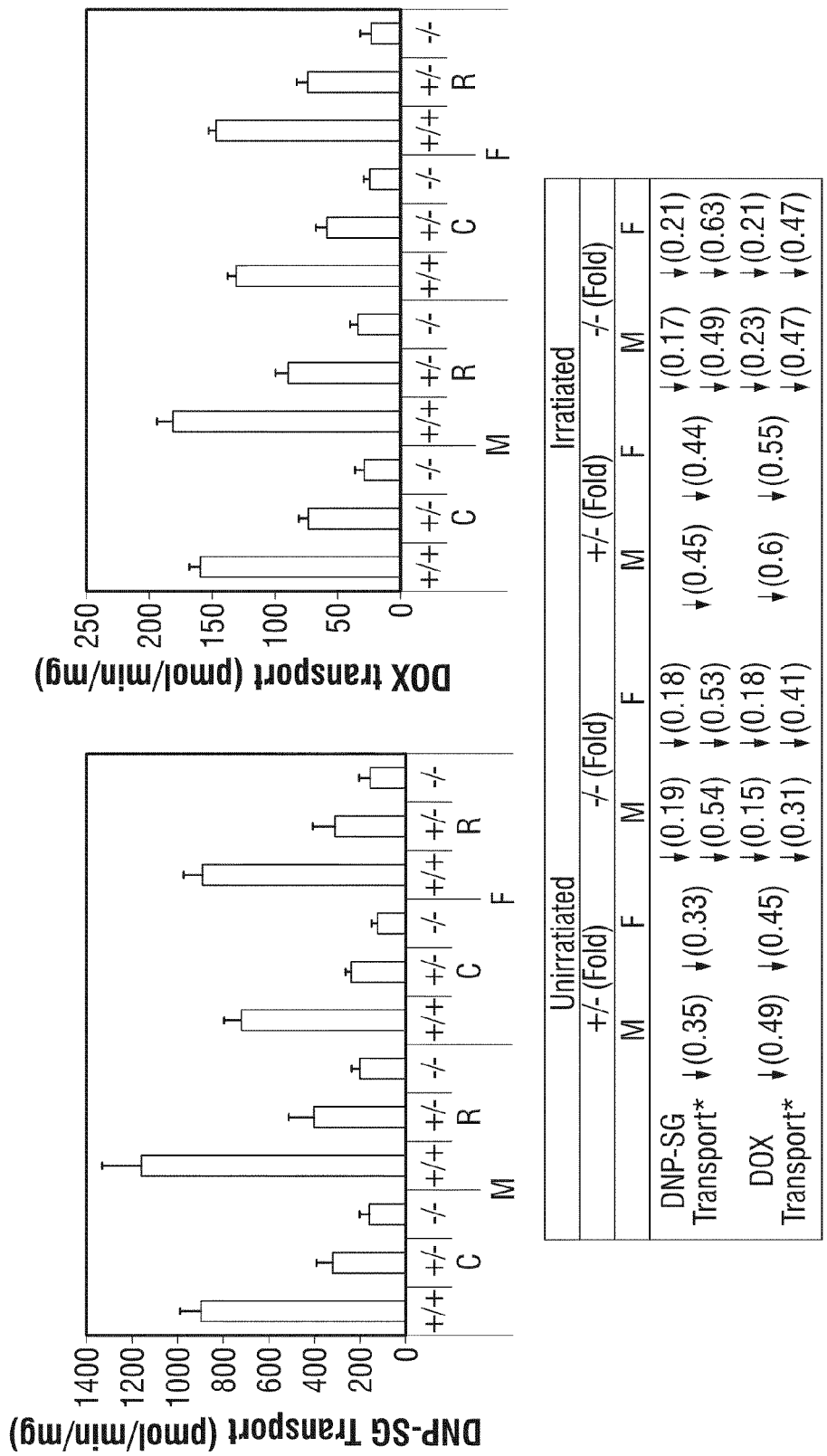
FIG. 10 depicts the effect of RIP1 knockout, radiation and gender on DOX and DNP-SG transport as embodied in one aspect of the present invention.

Consistent with the observed function of RalBP1 as a transporter of GS-E and DOX in cell culture studies, GS-E and DOX transport in membrane vesicles was found to be decreased in a stepwise fashion from the RIP1+/+, to RIP1+/−, to RIP1−/− mice (FIG. 10). For FIG. 10, DOX and DNP-SG transport was measured as previously described in crude membrane vesicles from mRALBP1+/+, +/− and −/− mice heart tissues (upper two panels, where C, and R represent un-irradiated and irradiated animals respectively, and M and F are male and female animals, respectively). Fold-changes shown in the TABLE 3 represent changes in +/− or −/− animals with respect to the +/+ animals. The values in the bold-font represent fold-change in the −/− animals as compared with the +/− animals. Blue font shows a decrease. All values presented were significant at p<0.01 by ANOVA.

A greater than 80% loss of total GS-E and DOX-transport activity was seen in the RIP1−/− mice. The differences in transport rates were statistically significantly lower in the RIP1+/− mice as compared with RIP1+/+, and in the RIP1−/− mice as compared with either RIP1+/− or RIP1+/+ mice. These findings demonstrate that RIP1 is the predominant GS-E and DOX transporter in mouse tissues.

As such, loss of RIP1 results in increased ambient levels of oxidative stress in tissues. To demonstrate, levels of two well-accepted markers of tissue oxidative stress, LOOH and TBARS, were assessed. These parameters were measured in homogenates from 7 tissues of each of 3 animals per group in all groups. The values obtained from the RIP1+/− and RIP1−/− mouse tissues were normalized to the corresponding values from RIP1+/+ mice to obtain fold differences. When analyzed in aggregate for all tissues (TABLE 3), significant (p<0.01) increase in both LOOH and TBARS was observed for both male and female animals in the RIP1+/− animals as compared with RIP1+/+ animals, and fold increase was greater in the RIP1−/− as compared with the RIP1+/+ animals. The increase seen in RIP1−/− was significant when compared with either RIP1+/+ or RIP1+/− mice. These findings conclusively demonstrated that progressive loss of RALBP1 results in progressive increase in tissue oxidative stress.

TABLE 3

Effect of RIP1 knockout on parameters reflecting oxidative stress

| | Unirradiated | | | | Irradiated (500 cGy) | | | |
|---|---|---|---|---|---|---|---|---|
| | +/− (Fold) | | −/− (Fold) | | +/− (Fold) | | −/− (Fold) | |
| Parameter | M | F | M | F | M | F | M | F |
| LOOH | ↑(1.32) | ↑(1.37) | ↑(1.94) | ↑(2.02) | ↑(1.62) | ↑(1.63) | ↑(2.10) | ↑(2.22) |
| | | | ↑(1.47) | ↑(1.48) | | | ↑(1.60) | ↑(1.63) |
| TBARS | ↑(1.18) | ↑(1.17) | ↑(1.68) | ↑(1.59) | ↑(1.43) | ↑(1.42) | ↑(1.94) | ↑(1.83) |
| | | | ↑(1.42) | ↑(1.35) | | | ↑(1.64) | ↑(1.56) |
| GSH | ↑(1.31) | ↑(1.48) | ↑(1.45) | ↑(1.59) | ↑(1.46) | ↑(1.58) | ↑(1.57) | ↑(1.76) |
| | | | ↑(1.10) | ↑(1.70) | | | ↑(1.20) | ↑(1.19) |
| GST | ↓(0.84) | ↓(0.85) | ↓(0.81) | ↓(0.82) | — | — | — | — |
| | | | | | | | — | ↑(1.11) |

TABLE 3-continued

Effect of RIP1 knockout on parameters reflecting oxidative stress

| | Unirradiated | | | | Irradiated (500 cGy) | | | |
|---|---|---|---|---|---|---|---|---|
| | +/- (Fold) | | -/- (Fold) | | +/- (Fold) | | -/- (Fold) | |
| Parameter | M | F | M | F | M | F | M | F |
| GPX | ↓(0.64) | ↓(0.79) | ↓(0.54)  ↓(0.85) | ↓(0.63)  ↓(0.81) | ↓(0.73) | ↓(0.88) | ↓(0.57)  ↓(0.90) | ↓(0.70) |
| GR | ↓(0.82) | ↓(0.84) | ↓(0.70)  ↓(0.85) | ↓(0.77)  ↓(0.91) | — | — | ↓(0.73)  ↓(0.89) | ↓(0.76)  ↓(0.91) |
| G6PD | ↓(0.82) | ↓(0.88) | ↓(0.78) | ↓(0.83) | — | ↑(1.19) | — | ↑(1.17)  ↑(1.33) |
| γ-GCS | — | — | — | ↓(0.79) | — | ↑(1.14) | — | ↓(0.91) |

For TABLE 3, methods for measurement of each parameter are those used by one of ordinary skill in the art. All parameters shown were measured in triplicate in brain, heart, lung, liver, kidney, intestine and spleen from each of 3 animals per group from 12 groups (3-genotype levels×2 gender levels×2 radiation levels). Radiation dose was 500 cGy administered, and animals were sacrificed on day 8. The values for fold-changes between +/+ versus either +/- or -/- are shown in the lighter font, and comparisons between +/- and -/- animals are in bold fonts. Increases with respect to control are in red font and arrows (↑), and decreases are in blue font and arrows (↓). Only those changes found to be significant by ANOVA ($p<0.01$) are presented, the missing values (-) were not significantly affected. Tables for results of individual tissues for unirradiated (FIG. 11) and X-irradiated (FIG. 12) animals, and results of one- two- and three-way ANOVA for significant interactions between gender, genotype and irradiation (FIG. 13) are shown.

GSH, the chief soluble cellular thiol and chemical antioxidant, was increased overall, in contrast to the GSH-linked antioxidant enzymes, which were generally decreased. These findings suggest that RIP1 may function, perhaps through regulation or Rho/Rac pathways, in up-regulation of these enzymes. Thus, increase in ambient LOOH could be explained as a secondary effect of the loss of RIP 1 due to decreased activities of GST, GPX, GR and G6PD, which normally metabolize LOOH and consume GSH. Increased GSH levels observed would thus be secondary to decreased consumption of GSH rather than increased synthesis, since the rate limiting enzyme for GSH-synthesis, γ-GCS, was unchanged or decreased. Analyses of these parameters by individual tissues supported this assertion (FIG. 11). The only tissue in which GSH, LOOH and TBARS were decreased was liver, where GST and GPX were increased. Changes in oxidative stress parameters and antioxidant enzymes were generally concordant for most tissues for any given parameter, and the degree of change was generally greater in the RIP1-/- animals as compared with the RIP1+/- animals. Taken together, these findings confirm that loss of RALBP1 results in global increase in tissue oxidative stress and changes in levels of GSH-linked antioxidant enzymes.

X-irradiation resulted in increase tissue oxidative stress with generally increased LOOH and TBARS in most tissues, and a greater degree of increase in RIP1-/- as compared with the RIP1+/- animals (FIG. 12). TBARS levels were, however, actually somewhat decreased in liver. With few exceptions, radiation caused a further decrease in expression of the GSH-linked enzymes. These findings are likely a combined effect of gender, genotype and irradiation which may affect the overall levels of these enzymes by causing varying levels of tissue damage (see results of ANOVA for one-way, two-way, and 3-way interactions in FIG. 13).

Whole mouse genome gene expression array was used to compare the effect of RIP1 knockout in heart tissue, an organ particularly severely affected in RIP1-/- animals. The microarray data was analyzed using commercially available software. The entire array of 34,560 genes was then filtered based on the criteria for stepwise up-regulation, which stated that there must be at least a 2 fold up-regulation on a given gene in the RIP1-/- mouse as compared with the RIP1+/+ mouse, and that the fold up-regulation between RIP1+/+ and RIP1+/- mouse multiplied by the fold up-regulation between the RIP1+/- and RIP1-/- mouse should be within 20% of that observed between RIP1+/+ and RIP1-/- mouse. This criteria was chosen on the basis of results with GSH-linked enzymes in which step-wise up or down-regulation of each enzyme between RIP1+/+ and RIP1+/- mouse multiplied by that between the RIP1+/- and RIP1-/- mouse was roughly equal to the change between RIP1+/+ and RIP1-/- mouse. Of the 7 genes which satisfied these criteria (TABLE 4), four were stress-induced or heat-shock induced proteins.

For TABLE 4, a murine genome array was used to compare RIP1+/+ versus RIP1+/-, RIP1+/+ versus RIP1-/-, and RIP1+/- versus RIP1-/-, each in duplicate and analyzed using IOBION software. Significant effects were selected by stipulating >2 fold increase, and by stipulating stepwise effects defined such that the up-regulation fold between RIP1+/+ versus RIP1-/- is within 20% of the product of the up-regulation folds of RIP1+/+ versus RIP1+/- and RIP1+/- versus RIP1-/-. The 7 up-regulated genes satisfying these criteria are presented.

TABLE 4

Genes up-regulated in heart tissue of RIP1 knockout

| Description | (+/+) vs. (+/-) | (+/-) vs. (-/-) | (+/+) vs. (-/-) |
|---|---|---|---|
| heat shock protein | 1.09 | 1.53 | 2 |
| heat shock protein 1, alpha | 1.38 | 1.36 | 2.19 |
| heat shock protein Hsp40 | 1.08 | 2.09 | 2.27 |
| 105-kDa heat shock protein | 1.12 | 2.57 | 2.35 |
| 25-kDa mammalian stress protein 1 | 1.41 | 1.54 | 2.21 |
| Stress-induced phosphoprotein 1 | 1.56 | 1.37 | 2.08 |
| insulin-like growth factor binding protein 5 | 2 | 1.72 | 3.62 |

Heat shock (stress) proteins (Hsp) are a family of proteins that vary in size (10 kDa to 110 kDa) and perform two essential functions within the cell. At homeostasis Hsp can behave as "chaperones" assisting proper folding of and proper compartmentalization of other proteins. Hsp can unfold and refold improperly folded proteins into the proper orientation or assist in targeting them for degradation. In a stress induced environment (temperature, xenobiotics, radiation, viral, and oxidative injury) where a higher likely hood of denatured proteins can exist, Hsp can mediate by either re-naturing the protein, degrading the protein, protecting the protein from becoming denatured, or transporting it to a compartment where it can be degraded. All of these actions assist the cell in maintaining its integrity. It is known that many Hsp are regulated by heat shock factor 1 (Hsf-1). Hsf-1 is a transcription factor that forms a ternary complex with some of the Hsp (inactive form). Upon stress, the Hsp is released and Hsf-1 is allowed to bind to DNA, which up-regulates and increases the Hsp production assisting in relief from the impending stress. It was recently discovered that Hsf1 forms a complex with Ral binding protein 1. Upon stress, the Ral signaling pathway is activated and RalBP1 is removed from the complex, which allows Hsf-1 to translocate into the nucleus where it up-regulated the production of stress proteins. Thus, RalBP1 binding to Hsf-1 serves to inhibit Hsf-1 from increasing heat-shock protein RNA transcription. The results herein are consistent with this conclusion since loss of RIP1 caused a stepwise up-regulation of heat shock proteins.

The present disclosure demonstrates stress-resistance mechanisms and the role of GS-E transport in these mechanisms. The stress-defense functions of RalBP1 have been strongly implicated in cell culture studies which show that it is induced within minutes of exposure to a variety of stressors including radiant energy and oxidants, and serves to decrease intracellular accumulation of GS-E. The formation of toxic and pro-apoptotic $\alpha,\beta$-unsaturated aldehydes is an obligate result of membrane lipid peroxidation which is known to occur in response to radiant and oxidative stress. GSTs catalyze the reversible conjugation of these aldehydes with GSH, and the resulting GS-E are potent inhibitors of GSTs as well as GR. Thus, the removal of these conjugates through further metabolism to mercapturic acids or transport from cells is critical, not only to prevent inhibition of these important GSH-linked oxidant defense enzymes, but also to prevent accumulation of the parent aldehydes that can arise from the reverse reaction favored by accumulation of these GS-E.

As such, RalBP1 serves a critical function in regulating cellular levels of these $\alpha,\beta$-unsaturated aldehydes which are known not only to be capable of cross-linking and denaturing proteins through formation of Schiffs bases and alkylation but also to be capable of triggering apoptosis once critical concentrations are reached. Induction of heat-shock proteins as a defense in the absence of RalBP1 is entirely consistent with the protein-denaturing effects of $\alpha,\beta$-unsaturated aldehydes. Since oxidative stress which results from hydroxyl-radical formation and formation of down-stream products of oxidation are accepted as chemical mechanisms for the toxic effects of radiant as well as chemical injuries, the function of RalBP1 in regulation of intracellular levels of these end-products of oxidation is entirely consistent with the role of RalBP1 as a prominent radiation-defense.

The linkage of RalBP1 to the Ral and Ras pathways and in particular to the Rho/Rac pathway, which is known to control stress responses, is also of fundamental significance and similar links have not been found for other transporters. Although clear evidence has been provided for the interaction of RalBP1 with these pathways, mechanistic explanations regarding how RalBP1 is involved in mediating a diverse array of functions has previously been far from clear. Through its protein-protein binding motifs in the C-terminal domain, it has clearly been shown to bind important signaling proteins including the AP2 clathrin adaptor protein, POB1, CDK1, and Hsp90 as well as Hsf1. Therefore, these proteins may be regulating some effector function of RalBP1. In addition, RalBP1 may be functioning as a regulator of these signaling proteins.

As described herein, RalBP1 has an effector function as an active nucleotidase which is capable of coupling ATPase activity with trans-membrane movement of several allocrites (see, also, Singhal, et al., *Int. J. Oncol.* 22:365-375, 2003; Awasthi, et al., 2000, supra; Awasthi, et al., 2001, supra; Awasthi, et al., *Int. J. Oncol.* 22:713-720, 2003a; Awasthi, et al., *Int. J. Oncol.* 22:721-732, 2003b; Awasthi, et al., 1994, supra; each incorporated herein by reference). RalBP1 has a C-terminal domain of RalBP1 and is found both in membrane as well as cytosol, it contains an active ATPase domain. The present disclosure demonstrates that RalBP1 is a modular protein containing multiple domains which may perform distinct functions at distinct intracellular sites.

The dramatic effect of RalBP1 liposomes in providing complete protection from radiation toxicity has direct implications for treatment of radiation toxicity. The very real risks of radiation poisoning as a result of a nuclear accident, nuclear bombs, or even terrorist attacks with "dirty-bombs," mandate the critical need for post-exposure treatment of radiation victims. As described herein, RalBP1 liposomes are excellent candidates for development as a radiation protective agent which may have broad applicability, particularly given that these liposomes are capable of delivering sustained levels of RalBP1 in all tissue, even brain. These findings also indicate that these liposomes may be useful as vehicles for delivery of drugs, antisense therapies and other therapies to the brain.

Thus, RalBP1 displays distinct transport properties as a nonselective transporter of neutral and charged compounds, is involved in multidrug resistance, and plays a role in modulating cellular signaling that affects cell proliferation and cell death. As a proteoliposome, RalBP1 may be provided to a mammal to protect against xenobiotic toxicity. Similarly, transfection of cells with an effective portion of RalBP1 that enables transporter activity will promote xenobiotic protection, including protection from environmental or other chemicals (e.g., stress-induced, drug delivered, physiologically-induced). Protection includes the treatment, inhibition, reduction, or prevention of accumulation in one or more cells of any chemical, that, when degraded, has the potential to damage these cells. This protection may be for environmental purposes, chemical procedures, or for mammals in need thereof.

The present disclosure also provides a method of reducing the effects of ionizing radiation on one or more cells in an organism comprising the step of contacting the organism with a Liposome further comprising RalBP1 or an effective portion of RalBP1.

Still another form of the present disclosure is a method of enhancing the export of toxic compounds from mammalian cells comprising the step of contacting one or more mammalian cells with a liposome further comprising RalBP1 or an effective portion of RalBP1.

The present disclosure also provides a method of transfecting mammalian cells to enhance the transport of toxic compounds comprising the step of contacting the organism with a liposome further comprising RalBP1 or an effective portion of RalBP1.

Another form of the present disclosure is a method of transfecting mammalian cells to enhance the resistance to ionizing radiation comprising the step of contacting one or more mammalian cells with a liposome further comprising RalBP1 or an effective portion of RalBP1.

In still another form, the present disclosure is a method of enriching mammalian cells to enhance their resistance to toxic compounds (including ionizing radiation) comprising the following step of contacting the organism with a liposome further comprising RalBP1 or an effective portion of RalBP1.

In addition, the present disclosure provides a proteoliposomal composition for the treatment of toxic compound exposure comprising a liposome further comprising RalBP1 or an effective portion of RalBP1 and a chemotherapeutic agent. Another form of the present disclosure is a proteoliposomal composition for the treatment of toxic compound exposure comprising a liposome further comprising RalBP1 or an effective portion of RalBP1 and an effective dose of radiation therapy.

In yet another form, the present disclosure is a protein composition that protects one or more cells against the harmful accumulation of toxic compounds comprising RalBP1 or an effective portion of RalBP1 and a ligand to RalBP1 that enhances transport activity of RalBP1.

The present disclosure also embodies a kit for protecting one or more cells in an organism from the accumulation of one or more toxic compounds comprising an effective dose of a liposome further comprising RalBP1 or an effective portion of RalBP1 and an instructional pamphlet.

The present disclosure also includes a method of enhancing the resistance of one or more mammalian cells to toxic compounds comprising the step of contacting one or more mammalian cells with a liposome further comprising RalBP1 or an effective portion of RalBP1.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims.

Example 1

Radiation Protection by RLIP76

Figure 14A:
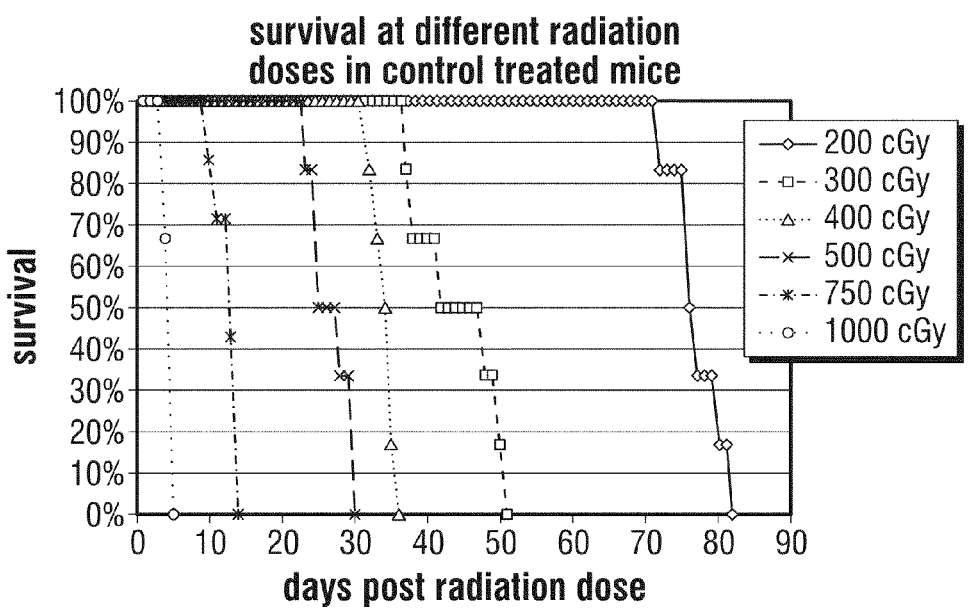
FIG. 14A depicts survival at different radiation doses in control treated mice.
Figure 14B:
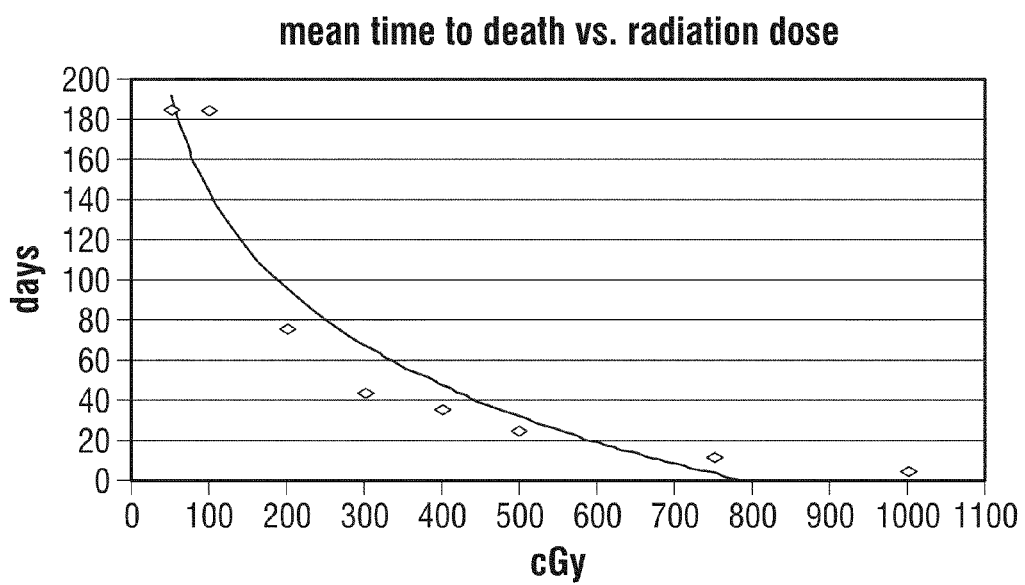
FIG. 14B depicts mean time to death versus radiation dose.

In all animal models, the relationship between radiation exposure and survival will vary depending upon experimental parameters, and so must be determined for each particular model with no treatment (control). FIG. 14A shows the baseline survival curves at different radiation doses for the C57/B16 mouse strain. As expected, survival times decrease with increasing radiation dose. A graph comparing the mean time to death as a function of radiation dose is shown in FIG. 14B.

In order to investigate whether RLIP76 could be effective when delivered within several hours after radiation exposure, a series of studies were conducted to explore the protective benefit of RLIP76 when given at varying doses, exposure levels, and times after exposure. One study compared the sensitivity of X-irradiation between RIP1+/+ and RIP1−/− mice and evaluated the effects of pharmacologic augmentation of RLIP76 in these animals. See Singhal et al., Int. J. Radiation Oncology Biol. Phys. 72(2):553-561 (2008).

In this study, mice from colonies of RLIP76+/+ and RLIP76−/− were used according to an Institutional Animal Care and Use Committee-approved protocol with assistance from trained animal facility personnel. RLIP76 liposomes were administered by intraperitoneal injection. Recombinant human RLIP76 was purified, authenticated, and reconstituted into artificial cholesterol:asolectin liposomes, as described in Awasthi et al., Biochemistry 39:9327-9334 (2000). For control liposomes, the addition of purified RLIP76 protein was omitted. Whole animal X-irradiation was administered using a Varian Clinac Linear accelerator (2100C; 6-MeV photon beams) with a dose range of 50-1,000 cGy. Mice were isolated to one side of the cage on top of 1.5 cm of super flab bolus and the field of treatment was centered on them. Total dose was split into two fractions, anterior and posterior, by rotating the accelerator gantry 180°.

Figure 15:
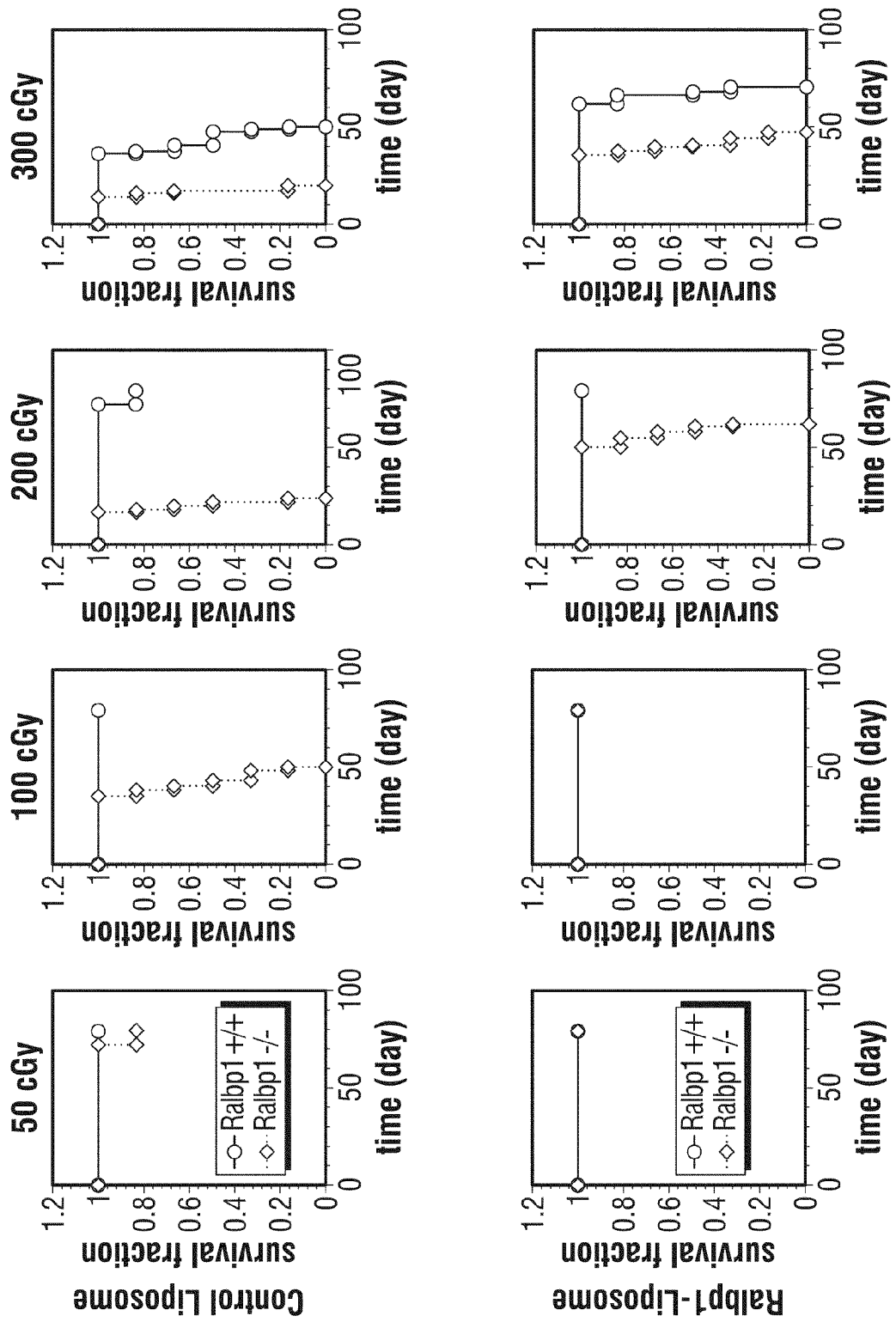
FIG. 15 depicts the effect of a single dose of RLIP76 on wild-type (+/+) RLIP76 mice (circles) and homozygous (−/−) RLIP76 mice (diamonds) exposed to 50 cGy, 100 cGy, 200 cGy, or 300 cGy whole body X-irradiation. The mice were further treated with control liposomes (no protein, Upper panels) or RLIP76-liposomes (Lower panels) at 14 hours after radiation exposure.

As shown in FIG. 15, RLIP offers protection from radiation toxicity in mice. C57 Black mice RLIP76+/+ (circles) and RLIP76−/− (diamonds) were weighed and randomized to radiation groups (50, 100, 200 or 300 whole body X-irradiation), and further randomized and treated by one intraperitoneal injection of 0.2 mL buffer containing either control liposomes (no protein, Upper panels) or RLIP76 liposomes (Lower panels) at 14 hours after radiation exposure. RLIP76 liposomes and control liposomes contained identical amounts of phospholipids and cholesterol, but the former had been reconstituted in the presence of purified RLIP76 such that each 0.2 mL contained 200 μg (2.6 nmol). After radiation exposure, mice were monitored for health and survival twice daily, and the survival curves are presented in FIG. 15.

As shown in FIG. 15, RLIP76−/− mice were more sensitive to radiation than RLIP76+1+ mice ($p<0.001$). The median lethal dose of RLIP76+/+ mice was 200-300 cGy, but for RLIP76−/− mice the median dose was 50-100 cGy. This indicates a dose modification factor of 3-4. The administration of RLIP76 liposomes at a single fixed dose of 200 μg recombinant RLIP76 protein has been previously shown to cause a significant increase in RLIP76 in mouse tissues, including the brain. See Awasthi et al., Cancer Res. 65:6022-6028 (2005). Here, when a dose identical to that used in the previous studies was administered 14 hours after radiation, we observed a remarkable improvement in survival of both RLIP76+/+ and RLIP76−/− mice. The protective effect of the liposomes was significant for the RLIP76+/+ mice at 300 cGy ($p<0.001$) and for RLIP76−/− mice at 100 cGy ($p<0.001$), 200 cGy ($p<0.001$), and 300 cGy ($p<0.001$). At the 50 cGy and 100 cGy dose, the RLIP76−/− mice treated with RLIP76 proteoliposomes had survival rates identical to that of RLIP76+/+ mice.

Figure 16:
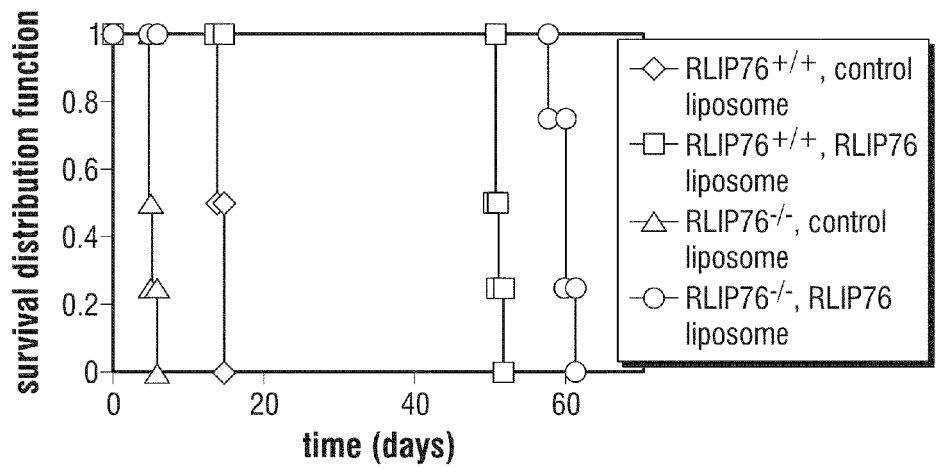
FIG. 16 depicts the effect of RLIP76 on survival after X-irradiation. Four wild-type (+/+) RLIP76 mice and four homozygous (−/−) RLIP76 mice were each exposed to 750 cGy X-irradiation and treated with control liposomes administered by i.p. injection (triangles, homozygous (−/−) RLIP76 mice; diamonds, wild-type (+/+) RLIP76 mice), or 400 μg RLIP76 liposomes administered by i.p. injection (circles, homozygous (−/−) RLIP76 mice; squares, wild-type (+/+) RLIP76 mice), given 12 hours after exposure.

In another study, four RLIP76+/+ mice were exposed to 750 cGy and treated with control liposomes administered by i.p. injection (FIG. 16, diamonds) or 400 μg RLIP76 liposomes administered by i.p. injection (FIG. 16, squares) given 12 hours after radiation exposure, and four RLIP76−/− mice were exposed to 750 cGy and treated with control liposomes administered by i.p. injection (FIG. 16, triangles) or 400 μg RLIP76 liposomes administered by i.p. injection (FIG. 16, circles) given 12 hours after radiation exposure. As shown in FIG. 16, administration of the RLIP76 liposomes increased the survival of the RLIP76−/− mice, but it also dramatically increased the survival of the RLIP76+/+ mice.

The finding that supplementation of RLIP76 levels above normal levels in mice is able to increase resistance of those mice to the toxic effects of radiation implies that RLIP76 functions as the "rate-limiting" step in this protective process. Therefore, increases in RLIP76 content may increase protection, using normal physiologic functions, in a dose and time responsive manner. Confirmation of this was established in studies investigating the effect of RLIP76 administration upon survival of irradiated mice under a variety of conditions.

Example 2

Radiation Protection by RLIP76 Liposomes Plus Anti-Oxidants

Unprotected RLIP76 protein is susceptible to proteolysis, rendering administration of the bare protein challenging. In this study, RLIP76 was administered in the form of lipid encapsulated proteoliposomes. In order to reduce or prevent oxidative degradation while awaiting administration, the buffer in which RLIP76 was reconstituted into liposomes contained an antioxidant, for example butylated hydroxytoluene (BTH). One or more other antioxidants could also be added to the liquid encapsulated proteoliposomes comprising RLIP76. Of note, BHT has been reported in the scientific literature as having a radioprotective effect on its own. Liposomes have also been used to deliver candidate radiation countermeasure drugs, but the ability of liposomes themselves to offer protection is not clear from the literature.

Given that lipid-based delivery of RLIP76 may improve stability of the protein in a pharmaceutical formulation, a complex of RLIP76 protein, liposomes, and antioxidants (such as BHT) was generated, and designated TO-80Cx (the 80 refers to the mean size of the liposomes of 80 nm, which classifies them as intermediate sized vesicles). Further designations include TO-80LA which refers to the liposomes constituted in buffer with antioxidants (BHT) and TO-80L which refers to liposomes in buffer without antioxidants or RLIP76 protein. Next, these complexes of RLIP76 proteoliposomes with antioxidants such as BHT were tested to determine whether they can confer protection and/or therapeutic effect for radiation toxicity in excess of the effects of liposomes and BHT alone or in combination.

Overall survival of 14-week old CD2F1 male mice weighing an average of 30.0 g was measured after exposure to 9.25 Gy gamma radiation from a cobalt 60 source at a dose rate of 0.60 Gy/min. The mice were grouped into cohorts of 16 mice/cohort and received multiple doses via intraperitoneal administration with TO-80Cx 50 µg (weight of RLIP76 protein)/mouse, or individual drug components of the same volume/concentration, using multiple time regimens and compared to controls. Survival of the mice was studied for 30 days.

Figure 17:
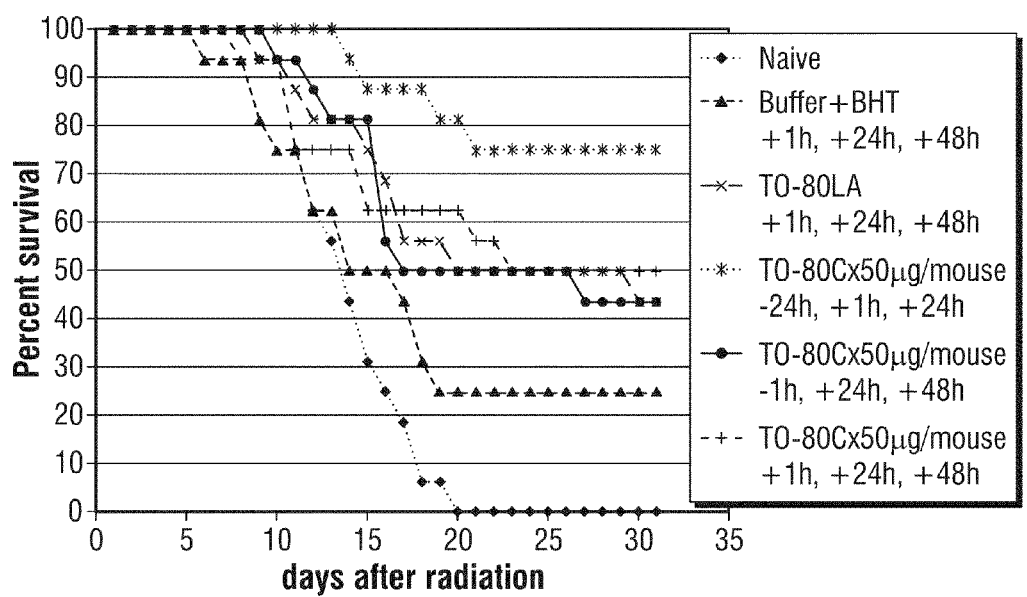
FIG. 17 shows overall survival rate of mice after gamma irradiation. Fourteen-week old CD2FI male mice were grouped into individual cohorts of 16 mice each and exposed to 9.25 Gy whole body gamma radiation delivered at 0.6 Gy/minute via cobalt60 source. The mice were treated with multiple doses of various formulations of liposomes, RLIP76 protein and antioxidant (BHT) via i.p. injection as shown.
Figure 18:
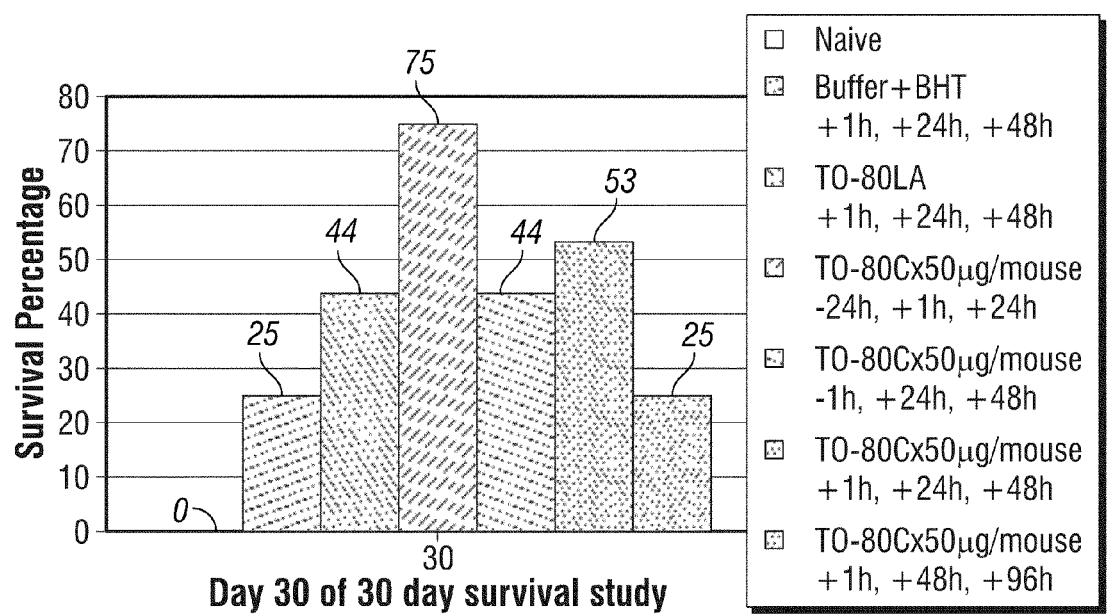
FIG. 18 is a different depiction of the percentage of mice from each cohort still alive at 30 days after gamma irradiation from FIG. 17.
Figure 19:
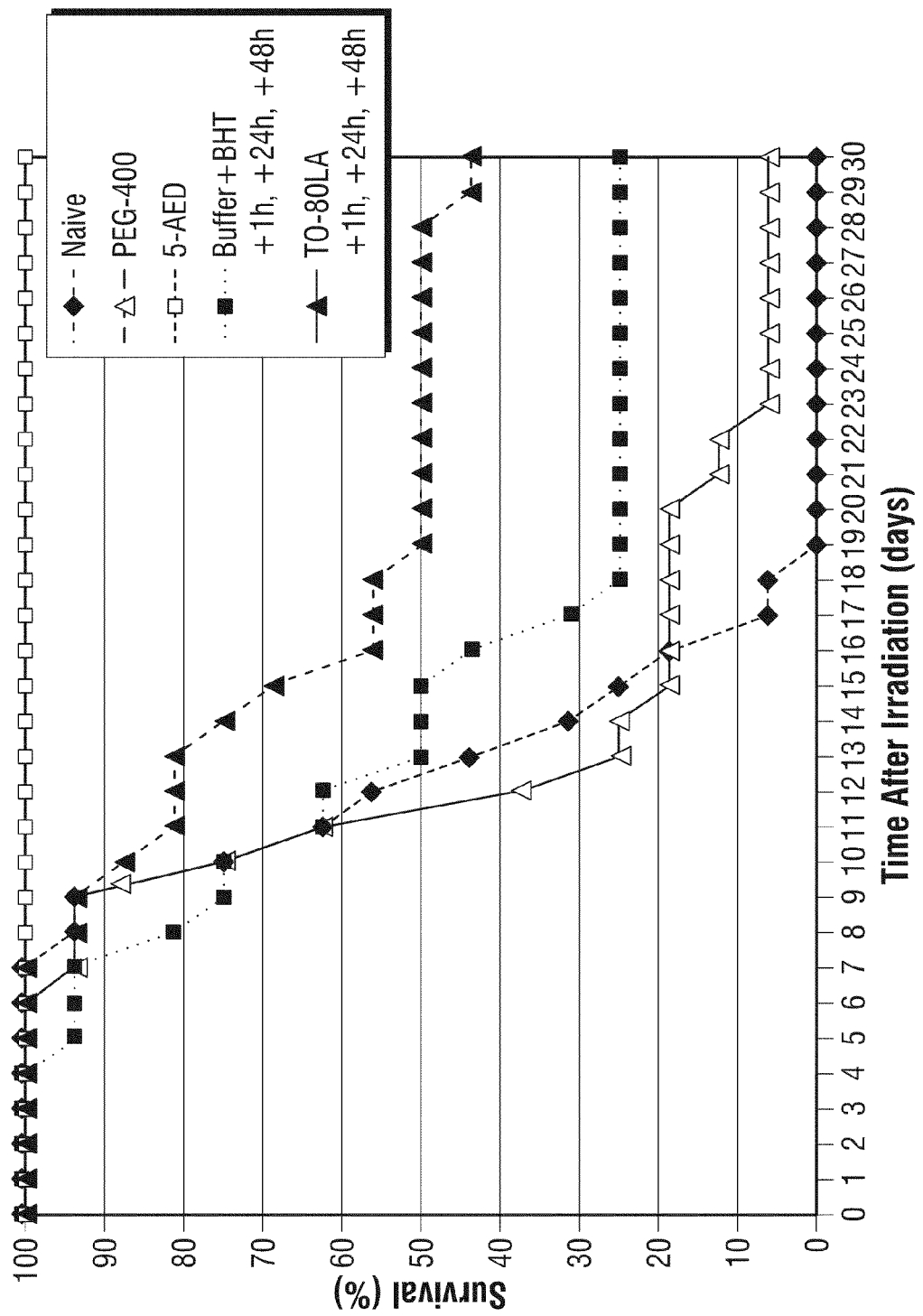
FIG. 19 shows the overall survival of additional cohorts of CD2F1 mice treated under the same conditions as described in FIG. 17 above, where the treatments are various delivery vehicles and controls delivered at the times specified after exposure. In the legend, 5-AED refers to 5-andrestenediol.
Figure 20:
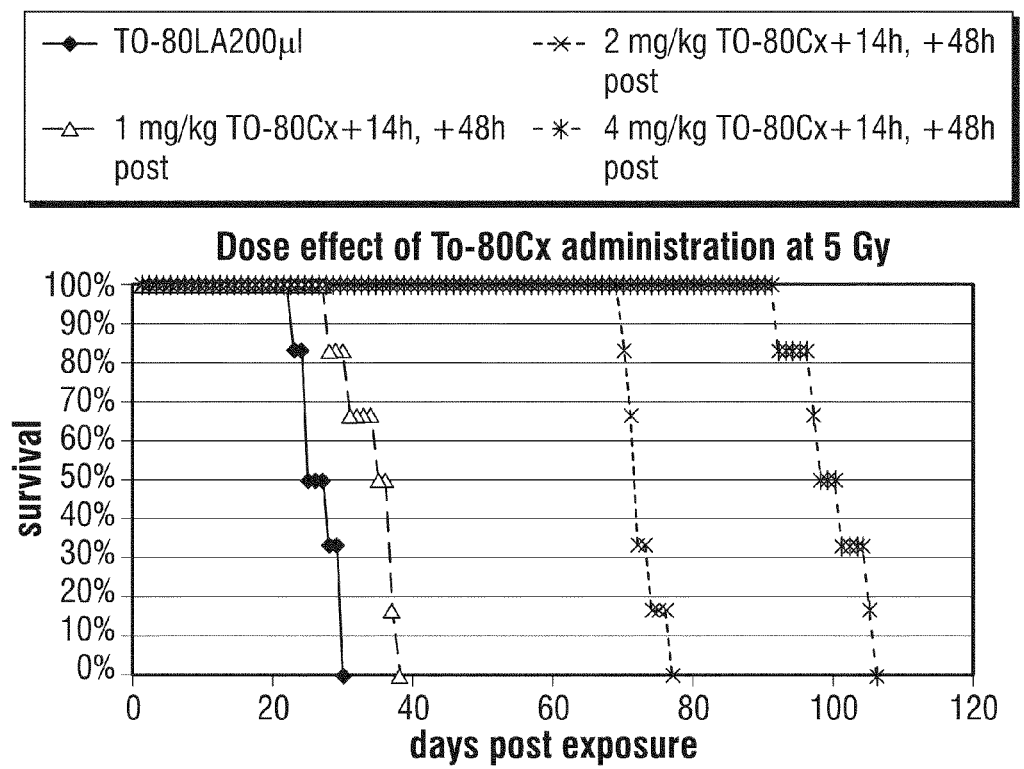
FIG. 20 shows overall survival rate of C57/Bl6 mice after a lower exposure to gamma irradiation, 5 Gy total body exposure, delivered via 6-MeV photon beam at a rate of 4 Gy/minute. In this experiment, the mice were treated with two doses of TO-80Cx administered 14 and 48 hours after exposure delivered via oral gavage. Dose levels shown are amount of RLIP76 protein contained in the volume of TO-80Cx delivered and are expressed as amount of protein per total body weight. The x-axis is the measure in days after radiation exposure and the y-axis is the percentage of each cohort alive on that day.

As shown in FIG. 17, maximum benefit was achieved with the full TO-80Cx complex given 24 hours prior to exposure. Lesser benefit in survival seen if administration was delayed until around the time of exposure in this experiment, although other experiments have found greater effect even if administration is delayed by some hours. This data is also shown in FIG. 18. In this experiment, BHT containing buffer alone yielded a small effect (Buffer+BHT) and a combination of liposomes and BHT yielded a greater effect (TO-80LA). In this experiment, TO-80LA had effects similar to TO-80Cx given peri-exposure. In a previous set of experiments, however, TO-80LA was markedly inferior to the full TO-80Cx at a lower total radiation exposure dose, as shown in FIG. 20. Interestingly, as shown in FIG. 19 a comparison of different delivery vehicles without RLIP76 showed that TO-80LA has some protective effect compared to BHT containing buffer alone, suggesting that the liposomes themselves may have some radioprotective effect.

Thus, each active component of TO-80Cx has some effect as a radioprotectant. However, maximum effect is seen with the full complex. The specific contribution in quantitative terms for liposomes or liposomes plus BHT remains variable and may depend upon the level of radiation exposure.

While specific alternatives to steps of the invention have been described herein, additional alternatives not specifically disclosed but known in the art are intended to fall within the scope of the invention. Thus, it is understood that other applications of the present invention will be apparent to those skilled in the art upon reading the described embodiment and after consideration of the appended claims and drawings.

What is claimed is:

1. A method of treating the effects of exposure to ionizing radiation in a mammal in need of such treatment, comprising administering an effective amount of RLIP76 protein to the mammal within 24 hours of exposure to the ionizing radiation.

2. The method of claim 1, wherein the mammal is human.

3. The method of claim 1, wherein the ionizing radiation is x radiation, gamma radiation, ultraviolet radiation, thermal radiation, nuclear radiation, or a combination thereof.

4. The method of claim 1, wherein the RLIP76 protein is administered within 24 hours before the exposure to the ionizing radiation.

5. The method of claim 1, wherein the RLIP76 protein is administered within 24 hours after the exposure to the ionizing radiation.

6. The method of claim 1 wherein the RLIP76 protein is administered at about the time of the exposure to the ionizing radiation.

7. The method of claim 1, wherein RLIP76 protein is comprised within a liposome.

8. The method of claim 1, wherein the RLIP76 protein is administered in one or more doses to the mammal.

9. The method of claim 8, wherein at least a first dose of the RLIP76 protein is administered within 24 hours before the exposure to the ionizing radiation.

10. The method of claim 8, wherein at least a first dose of the RLIP76 protein is administered within 24 hours after the exposure to the ionizing radiation.

11. The method of claim 8, wherein at least a first dose of the RLIP76 protein is administered at about the time of the exposure to the ionizing radiation.

12. The method of claim 9, further comprising administering to the mammal at least a second dose of the RLIP76 protein within 24 hours after the exposure to the ionizing radiation.

13. The method of claim 12, wherein the first dose and the second dose comprise about the same amount of the RLIP76 protein.

14. The method of claim 12, wherein the first dose and the second dose comprise different amounts of the RLIP76 protein.

15. The method of claim 1, wherein the RLIP76 protein is administered in one or more doses to the mammal within 24 hours before the exposure to the ionizing radiation.

16. The method of claim 15, further comprising administering to the mammal one or more doses of the RLIP76 protein within 24 hours after the exposure to the ionizing radiation.

17. A method of treating the effects of exposure to ionizing radiation in a mammal in need of such treatment, comprising administering one or more doses of a proteoliposomal composition comprising an effective amount of RLIP76 protein or an effective portion thereof to the mammal within 24 hours of exposure to the ionizing radiation.

18. The method of claim 17, wherein said proteoliposomal composition comprises between about 0.5 mg/kg body weight and about 14 mg/kg body weight of the RLIP76 protein.

19. The method of claim 17, wherein the proteoliposomal composition further comprises a lectin, a glycolipid, a phospholipid, or a combination thereof.

20. The method of claim 17, wherein the RLIP76 protein is a recombinant protein.

21. The method of claim 17, wherein the one or more doses of proteoliposomal composition is administered subcutaneously, intravenously, topically, orally, non-orally, or a combination thereof.

22. The method of claim 21, wherein the one or more doses of proteoliposomal composition is administered orally.

23. A method of treating the effects of exposure to ionizing radiation in a mammal in need of such treatment, comprising administering (a) at least a first dose of proteoliposomal composition comprising an effective amount of RLIP76 protein to the mammal before exposure to the ionizing radiation, and (b) at least a second dose of proteoliposomal composition comprising an effective amount of RLIP76 protein to the mammal after exposure to the ionizing radiation.

24. The method of claim 23, wherein the mammal is human.

25. The method of claim 23, wherein the ionizing radiation is x radiation, gamma radiation, ultraviolet radiation, thermal radiation, or nuclear radiation, or a combination thereof.

26. The method of claim 23, wherein the first dose is administered within 24 hours before the exposure to the ionizing radiation.

27. The method of claim 23, wherein the second dose is administered within 24 hours after the exposure to the ionizing radiation.

28. The method of claim 27, further comprising administering to the mammal at least a third dose of proteoliposomal composition comprising an effective amount of RLIP76 protein to the mammal more than 24 hours after the exposure to the ionizing radiation.

29. The method of claim 23, wherein the first dose and the second dose comprise about the same amount of the RLIP76 protein.

30. The method of claim 23, wherein the first dose and the second dose comprise different amounts of the RLIP76 protein.

* * * * *